(12) United States Patent
Klein et al.

(10) Patent No.: US 6,521,641 B1
(45) Date of Patent: Feb. 18, 2003

(54) MALE ANTI-FERTILITY AGENTS

(75) Inventors: Elliott S. Klein, Marina Del Rey, CA (US); Yang-Dar Yuan, Irvine, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 74 days.

(21) Appl. No.: 09/591,253

(22) Filed: Jun. 9, 2000

Related U.S. Application Data

(63) Continuation-in-part of application No. 09/405,748, filed on Sep. 27, 1999, now abandoned.
(60) Provisional application No. 60/103,507, filed on Oct. 8, 1998.

(51) Int. Cl.$^7$ .................. A61P 15/16; A61K 31/352; A61K 31/4353; A61K 31/38; A61K 31/192
(52) U.S. Cl. .................. 514/333; 514/332; 514/337; 514/456; 514/841; 514/454; 514/437; 514/432; 514/411; 514/412; 514/438; 514/468
(58) Field of Search .................. 514/333, 337, 514/332, 456, 454, 841–482, 570, 437, 432, 411, 412, 438, 468

(56) References Cited

U.S. PATENT DOCUMENTS

| | | |
|---|---|---|
| 4,134,918 A | 1/1979 | Bey et al. |
| 4,182,891 A | 1/1980 | Metcalf et al. |
| 4,677,193 A | 6/1987 | Rivier et al. |
| 5,501,855 A | 3/1996 | Talwar et al. |
| 5,728,846 A | 3/1998 | Vuligonda et al. |
| 5,744,448 A | 4/1998 | Kelton et al. |
| 5,753,231 A | 5/1998 | Herr et al. |
| 5,776,699 A | 7/1998 | Klein et al. |

FOREIGN PATENT DOCUMENTS

| | | |
|---|---|---|
| WO | WO 94/14777 | 7/1994 |
| WO | WO 94/19370 | 9/1994 |
| WO | WO 98/24901 | 6/1998 |

OTHER PUBLICATIONS

Eskild, W. & Hansson, V., "Vitamin A Functions in the Reproductive Organs in Vitamin A in Health Disease" pp. 531–558 (Blomhoff, R. ed., 1994).
Huang et al, 112, No. 4, "Endocrine Changes Associated with Germ Cell Loss during Vitamin A–Induced Recovery of Spermatogenesis" Endocrinology, pp. 1163–1171 (1983).
Evans, "The Steroid and Thyroid Hormone Receptor Superfamily", Science, Vol. 240: pp. 889–895 (1988).
Mangelsdorf et al, "The Retinoid Receptors" in *The Retinoids: Biology, Chemistry and Medicine* Ch. 8 (Sporn et al, eds. 2d ed., Raven Press Ltd. 1994).
Nagpal et al, "Retinoids as Anti–Cancer Agents", Current Pharm. Design, 1996, 2, pp. 295–316.
Mather et al, pp. 18–28, Ch. 2, "Effects of Retinoids on Testicular Cell Function in Vitro", *Retinoids and cell Differentiation* (1986).
Kastner et al, "Abnormal spermatogenesis in RXRβ mutant mice", Genes & Development 10: pp. 80–92 (1996).

*Primary Examiner*—Edward J. Webman
(74) *Attorney, Agent, or Firm*—Carlos A. Fisher; Martin A. Voet; Robert J. Baran

(57) ABSTRACT

Methods and compositions for inhibiting or preventing spermatogenesis in a male mammal. Also disclosed are compounds and formulations for use in such methods.

23 Claims, No Drawings

MALE ANTI-FERTILITY AGENTS

This application is a continuation in part of application Ser. No. 09/405,748, filed Sep. 27, 1999, now abanboned, which claimed priority under 35 USC 119(e) to provisional application Serial No. 60/103,507, filed Oct. 8, 1998. Both of these applications are incorporated by reference herein.

FIELD OF THE INVENTION

The present invention concerns methods and compositions for inhibiting or blocking fertility in a male mammal by the administration of a retinoid or retinoid derivative that is able to act as an antagonist or inverse agonist of a retinoic acid receptor (RAR). The effect is reversible upon cessation of treatment with the RAR antagonist or inverse agonist.

BACKGROUND OF THE INVENTION

The prevention of unplanned pregnancy in humans and other mammals is of continuing concern for both the developing and the developed world. A variety of methods and products have been proposed or developed for the prevention of pregnancy; these products include: surgical sterilization, condoms, birth control pills containing progestin or a combination of progestin and estrogen, subdermal implants containing delayed release forms of progesterone, intrauterine devices, spermicidal creams or gels, and intravaginal barriers such as sponges or diaphragms.

These various methods each have certain advantages and certain drawbacks. The most common non-surgical birth control method in the United States is the birth control pill ("the Pill"), which contains synthetic progestin and estrogen; synthetic hormones similar to those produced naturally in a woman's body. The Pill works primarily by suppressing the release of eggs from a woman's ovaries.

Within two years after its introduction in 1960, approximately 1.2 million women were using oral birth control, and by 1973, about 10 million women were using the Pill. However, in recent years questions have arisen about the health risks involved in continued long term use of contraceptive hormones. There have been reports of increased risk of certain forms of cancer, such as breast and cervical cancer, though the use of the Pill.

Surgical sterilization, whether through tubal ligation or vasectomy, is nearly 100% effective, but is only sometimes reversible. Reversal of surgical sterilization usually requires further surgery.

Condoms, made of either synthetic polymer materials or animal skin, are less effective n birth control pills and their effectiveness is further subject to subversion through the possibility that small breaks may be present, permitting leakage of semen. Additionally, the use of a condom requires the affirmative action of the male, usually immediately prior to the initiation of sexual intercourse and some men report a loss of sensation through the use of condoms. Hence, subject noncompliance is also an issue in the use of condoms.

Subdermal implants, such as the NORPLANT® implant device, are quite effective contraceptive means. The implant comprises a set of silicone rods that are inserted under the skin of the upper arm. The implant contains hormones, such as progestin, levonorgestrel and progesterone, that are slowly released over a period of time of up to five years. Side effects may be similar to those involved in the use of birth control pills, and include a risk of developing ovarian cysts. Additionally, while the implant can be removed, the procedure is difficult even for skilled surgeons due to the formation of scar tissue around the implant.

Intrauterine devices (IUDs) are small devices that are typically either made of copper or impregnated with progesterone. These must be inserted (and removed) by a doctor. Depending on the design, the devices appear to interfere with sperm motility or the implantation of the fertilized egg in the uterine wall. Side effects can include cramps, backache, spotting, or heavy periods, and women may have an increased risk of ectopic pregnancy or infertility. IUDs are usually not recommended for women who have not had children or who think they will have children in the future due to these latter risks. Normally, the contraceptive effects are reversible upon removal of the device.

Barriers such as diaphragms and sponges are usually used in conjunction with a spermicidal cream, foam, or gel. The effectiveness of such devices is between about 90% and about 95%. The user can insert them as long as a number of hours before sexual intercourse, and the effects are temporary; if pregnancy is subsequently desired, the woman can discontinue their use with a concomitant return of fertility.

With the exception of surgical sterilization and the use of condoms, all of the methods in common use affect female fertility with no effect on male fertility. As mentioned above, the former of these methods is irreversible and the latter is neither inherently as effective as other methods, nor is compliance as high. A male contraceptive that is not required to be applied immediately prior to intercourse would provide a contraceptive alternative to the traditional methods of contraception.

A number of compositions have been proposed for use as a male contraceptive. Thus, U.S. Pat. No. 5,501,855, to Talwar et al., describes application of neem (*Azadirachta indica*) oil by injection to the vas deferens in an amount effective to block the fertility of the male by spermatogenic arrest. A single injection was reported to be effective to block fertility over the 9 month period of observation reported in the '855 patent.

U.S. Pat. No. 4,677,193 and International Patent Publication No. WO 94/19370, both to Rivier et al., describe a hypothalamic peptide hormone (termed GnRH) that functions to trigger the release of gonadotropic hormones such a luteinizing hormone (LH) and follicle-stimulating hormone (FSH) in the female. These references also mention that antagonists of GnRH are effective to arrest spermatogenesis in male mammals. This treatment apparently requires supplemental testosterone to be provided with the treatment in order to maintain libido.

U.S. Pat. No. 5,744,448, to Kelton et al., describes the cloning, expression, and purification of human FSH receptor, or mutants or fragments thereof that retain the ability to bind FSH. One possible use of the FSH receptor is described as a method for preventing spermatogenesis in a male patient.

U.S. Pat. No. 4,182,891, to Metcalf et al., and U.S. Pat. No. 4,134,918, to Bey et al. describe compounds said to be useful in inhibiting spermatogenesis. The '891 patent describes acetylenic derivatives of amino acids, and the '918 patent describes halomethyl derivatives of amines.

International Patent Publication No. WO 97/24901, to Bandman et al., describes the amino acid sequence of a polypeptide termed Lung Growth Factor Variant (LGFV), which is said to play a role in various physiological processes, including spermatogenesis.

U.S. Pat. No. 5,753,231, to Herr, et al., describes a female contraceptive vaccine prepared from antibodies raised to a recombinant primate acrosomal sperm antigen. The vaccine elicits an anti-sperm immune response, resulting in inhibition of fertilization. Also described are contraceptive compositions containing such an antibody in a carrier for vaginal application.

None of the references cited herein are admitted in any manner to be prior art against the present application.

SUMMARY OF THE INVENTION

The present invention concerns the discovery that certain agents that are able to block the binding of retinoic acid (RA) or other RAR ligands to RAR receptors, and thereby prevent activation of RARs, are also able to inhibit spermatogenesis in a male mammal.

It has been known for some time that among the various results of a severe vitamin A (retinol) deficiency in mammals is sterility and blindness. See Eskild, W. & Hansson V., *Vitamin A Functions in the Reproductive Organs in Vitamin A in Health and Disease* 531 (Blomhoff, R. ed., 1994) (hereinafter Eskild). A complete deficiency in retinoids is fatal. Administration of retinoic acid in the absence of retinol can alleviate many of the symptoms of vitamin A deficiency, giving rise to blind and sterile animals that remain otherwise healthy.

Researchers have also noted that treatment of vitamin A-deficient rats (in which there was a complete spermatogenic arrest) with vitamin A replacement results in restoration of normal spermatogenesis; reinitiation of spermatogenesis occurs in rats within 24–48 hours following vitamin A replacement. Huang, et al., 112 Endocrinology 1163–71 (1983), incorporated by reference herein.

A vast array of specific metabolic, developmental, and catabolic processes appear to be directly or indirectly regulated in vivo by comparatively small molecules such as steroids, retinoids and thyroid hormones. The mechanism whereby a single such compound can contribute to the regulation of numerous different cellular events was the subject of much speculation until relatively recently, when it was discovered that these compounds each share the ability to bind to transcriptionally active proteinaceous receptors. These protein receptors, in turn, are able to bind specific cis-acting nucleic acid regulatory sequence regions, termed response elements or RE's, located upstream of the coding sequence of certain genes and to activate the transcription of these genes. Thus, these proteinaceous receptors can serve as specific, ligand-dependent regulators of gene transcription and expression.

The amino acid sequences of these various receptors were quickly found to share regions of homology, thus making each such receptor a member of a family of ligand-modulated receptor molecules. This family has been termed the steroid superfamily of nuclear hormone receptors; nuclear, because the receptors are usually found in high concentration in the nucleus of the cell, although it is not clear that these are always the only relevant locations in which these receptors are found, or that transcriptional activation is the only activity that the receptors possess.

Further study of the structural and functional relationship between the nuclear hormone receptors has shown certain characteristics in common between them in addition to sequence. homology. See e.g., Evans et al. *Science* 240:889–895 (1988). As stated above, the nuclear hormone receptors are able to bind to cis-acting regulatory elements present in the promoters of the target genes. The glucocorticoid, estrogen, androgen, progestin, and mineralcorticoid receptors have been found to bind as homodimers to specific response elements organized as inverted repeats.

Another class of nuclear hormone receptors, which includes the retinoid receptor RAR (retinoic acid receptor), the thyroid receptor, the vitamin D receptor, the peroxisome proliferator receptor, and the insect ecdysone receptor bind their response element as a heterodimer in conjunction with the retinoid X receptor (RXR), which in turn is positively activated by 9-cis retinoic acid. See Mangelsdorf, et al., *The Retinoid Receptors* in *The Retinoids: Biology, Chemistry and Medicine* Ch.8 (Sporn et al., eds. 2d ed., Raven Press Ltd. 1994); Nagpal and Chandraratna, *Current Pharm. Design* 2:295–316 (1996), which are both incorporated by reference herein. The retinoid receptors RAR and RXR, like many nuclear receptors, exist as a number of subtypes (RARα, RARβ, RARγ, and RXRα, RXRβ, and RXRγ). Additionally, each subtype may exist in different soforms.

The present Applicants have surprisingly discovered that administration of an RAR antagonist or RAR inverse agonist results in the arrest of spermatogenesis in male mammals. By "antagonist" is meant that an agent is able to bind to the retinoic acid binding site of an RAR, thereby blocking the binding of retinoic acid to, and activation of the RAR. By "inverse agonist" is meant an agent able to suppress the el o activity (homo- or heterodimerization and trans-acting transcriptional control of various genes whose regulation is normally responsive to RAR modulation). A compound will normally be an RAR antagonist if it is an inverse agonist, but the converse is not necessarily true.

The spermatogenetic arrest resulting from treatment of a male mammal with an effective amount of an RAR antagonist or inverse agonist is not accompanied by most other symptoms of hypovitaminosis A, such as blindness, abnormal growth or susceptibility to infectious disease. Testosterone levels appear to remain normal; thus the preferred agents do not significantly affect male libido and sexuality.

This, these compositions have applicability as agents for veterinary or therapeutic application as a male contraceptive.

Some examples of structures and methods of making and using preferred RAR antagonists and inverse agonists are provided in U.S. Pat. No. 5,776,699 and U.S. patent application Ser. Nos. 08/998,319, 08/880,823, and 08/840,040 which are all incorporated by reference herein in their entirety.

Many of the following compounds are included in one or more of these applications.

A class of preferred compounds has the structure:

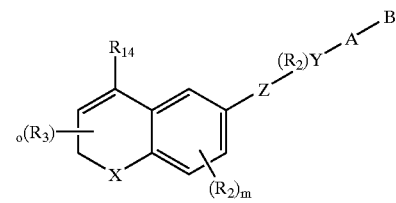

wherein
X is S, O, NR' where R' is H or alkyl of 1 to 6 carbons, or
X is [C(R$_1$)$_2$]$_n$ where R$_1$ is independently H or alkyl of 1 to 6 carbons, and n is an integer between, and including, 0 and 2, and;
R$_2$ is hydrogen, lower alkyl of 1 to 6 carbons, F, Cl, Br, I, CF$_3$, fluoro substituted alkyl of 1 to 6 carbons, OH, SH, alkoxy of 1 to 6 carbons, or alkylthio of 1 to 6 carbons, and;

$R_3$ is hydrogen, lower alkyl of 1 to 6 carbons or F, and;

m is an integer having the value of 0–3, and;

o is an integer having the value of 0–3, and;

Z is

—C≡C—,

—N=N—,

—N=CR$_1$—,

—CR$_1$=N,

—(CR$_1$=CR$_1$)n'— where n' is an integer having the value 0–5,

—CO—NR$_1$—,

—CS—NR$_1$—,

—NR$_1$—CO,

—NR$_1$—CS,

—COO—,

—OCO—;

—CSO—;

—OCS—;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or when Z is —(CR$_1$=CR$_1$)n'— and n' is 3, 4 or 5 then Y represents a direct valence bond between said (CR$_2$=CR$_2$)$_{n'}$ group and B;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COOR$_8$, CONR$_9$R$_{10}$, —CH$_2$OH, —CH$_2$OR$_{11}$, CHO, CH(OR$_{12}$)$_2$, CHOR$_{13}$O, —COR$_7$, CR$_7$(OR$_{12}$)$_2$, CR$_7$OR$_{13}$O, or tri-lower alkylsilyl, where $R_7$ is an alkyl, cycloalkyl or alkenyl group containing 1 to 5 carbons, $R_8$ is an alkyl group of 1 to 10 carbons or trimethylsilylallyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $R_{14}$ is (R$_{15}$)$_r$-phenyl, (R$_{15}$)$_r$-naphthyl, or (R$_{15}$)$_r$-heteroaryl where the heteroaryl group has 1 to 3 heteroatoms selected from the group consisting of O, S and N, r is an integer having the values of 0–5, and $R_{15}$ is independently H, F, Cl, Br, I, NO$_2$, N(R$_8$)$_2$, N(R$_8$)COR$_8$, NR$_8$CON(R$_8$)$_2$, OH, OCOR$_8$, OR$_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons.

Another preferred class of compounds has the structure:

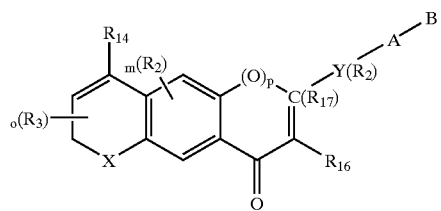

wherein

X is S, O, NR' where R' is H or alkyl of 1 to 6 carbons, or

X is [C(R$_1$)$_2$]$_n$ where $R_1$ is independently H or alkyl of 1 to 6 carbons, and n is an integer between, and including, 0 and 2, and;

$R_2$ is hydrogen, lower alkyl of 1 to 6 carbons, F, Cl, Br, I, CF$_3$, fluoro substituted alkyl of 1 to 6 carbons, OH, SH, alkoxy of 1 to 6 carbons, or alkylthio of 1 to 6 carbons, and;

$R_3$ is hydrogen, lower alkyl of 1 to 6 carbons or F, and;

m is an integer having the value of 0, 1, 2, or 3, and;

o is an integer having the value of 0, 1, 2, or 3, and;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, and;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, or tri4ower alkylsilyl, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and;

$R_{14}$ is (R$_{15}$)$_r$-phenyl, (R$_{15}$)$_r$-naphthyl, or (R$_{15}$)$_r$-heteroaryl where the heteroaryl group has 1 to 3 heteroatoms selected from the group consisting of O, S and N, r is an integer having the values of 0,1, 2, 3, 4 or 5, and;

$R_{15}$ is independently H, F, Cl, Br, I, NO$_2$, N(R$_8$)$_2$, N(R$_8$)COR$_8$, NR$_8$CON(R$_8$)$_2$, OH, OCOR$_8$, OR$_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons, and;

$R_{16}$ is H, lower alkyl of 1 to 6 carbons, and;

$R_{17}$ is H, lower alkyl of 1 to 6 carbons, OH or OCOR$_{11}$, and;

p is 0 or 1, with the proviso that when p is 1 then there is no R17 substituent group, and m is an integer between, and including, 0 and 2.

A further preferred class of compounds is the class of the structure:

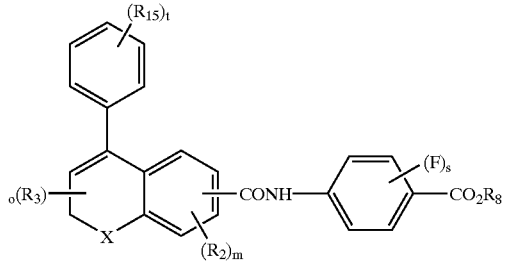

where

X is $C(R_1)_2$ or O, and;

$R_1$ is H or alkyl of 1 to 6 carbons, and;

$R_2$ is lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons, and;

m is an integer having the value of 0–3, and;

$R_3$ is lower alkyl of 1 to 6 carbons of F, and;

o is an integer having the value of 0–3, and;

s is an integer having the value of 1–3, and;

$R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, and;

$R_{15}$ is independently H, F, Cl, Br, I, $NO_2$, $N(R_8)_2$, $COR_8$, $NR_8CON(R_8)_2$, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, an alkynyl group having 1 to 10 carbons and 1 to 3 triple bonds, or a trialkylsilyl or trialkylsilyloxy group where the alkyl groups independently have 1 to 6 carbons, and;

t is an integer having the values of 0, 1, 2, 3, 4, or 5, and;

the CONH group is in the 6 or 7 position of the benzopyran, and in the 2 or 3 position of the dihydronaphthaline ring, or a pharmaceutically acceptable salt of said compound.

Another preferred class of compounds is that of the structure:

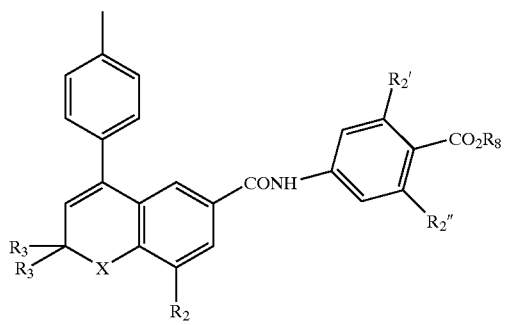

where

X is $C(CH_3)_2$ or O, and;

$R_2$ is H or Br, and;

$R_{2'}$ and $R_{2''}$ independently are H or F, and;

$R_3$ is H or $CH_3$, and;

$R_8$ H, lower alkyl of 1 to 6 carbons, or a pharmaceutically salt of said compound.

A further class of such compounds has the structure:

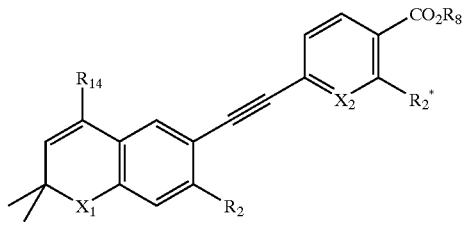

where $X_1$ is S or O;

$X_2$ is CH or N;

$R_2$ is H, F, $CF_3$ or alkoxy of 1 to 6 carbons;

$R_2$*H, F, or $CF_3$;

$R_8$ is H, or lower alkyl of 1 to 6 carbons;

$R_{14}$ is unsubstituted phenyl, thienyl or pyridyl, or phenyl, thienyl or pyridyl substituted with one to three $R_{15}$ groups, where $R_{15}$ is lower alkyl of 1 to 6 carbons, chlorine, $CF_3$, or alkoxy of 1 to 6 carbons, or a pharmaceutically acceptable salt of said compound.

In yet another preferred embodiment of the invention, the compound has the structure:

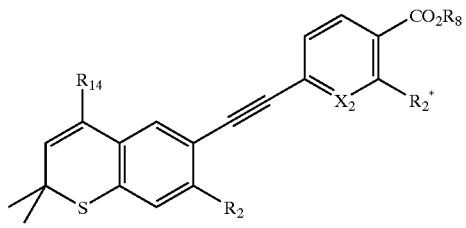

wherein $X_2$ is CH or N, and;

$R_2$ is H, F, or $OCH_3$, and;

$R_2$*H or F, and;

$R_8$ is H, or lower alkyl of 1 to 6 carbons, and;

$R_{14}$ is selected from the group consisting of phenyl, 4-(lower-alkyl)phenyl, 5-(lower alkyl)-2-thienyl, and 6-(lower alkyl)-3-pyridyl where lower alkyl has 1 to 6 carbons, or a pharmaceutically acceptable salt of said compound.

A further preferred class of such compounds has the structure:

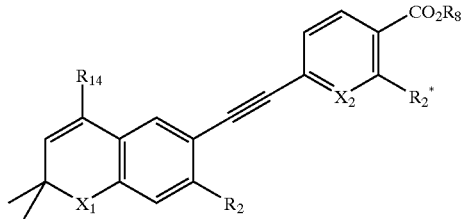

where $X_1$ is S or O;

$X_2$ is CH or N;

$R_2$ is H, F, $CF_3$ or alkoxy of 1 to 6 carbons;

$R_2^*$H, f, or $CF_3$;

$R_8$ is H, or lower alkyl of 1 to 6 carbons;

$R_{14}$ is unsubstituted phenyl, thienyl or pyridyl, or phenyl, thienyl or pyridyl substituted with one to three $R_{15}$ groups, where $R_{15}$ is lower alkyl of 1 to 6 carbons, chlorine, $CF_3$, or alkoxy of 1 to 6 carbons, or a pharmaceutically acceptable salt of said compound.

In an event more preferred embodiment of the invention, the compound has the structure:

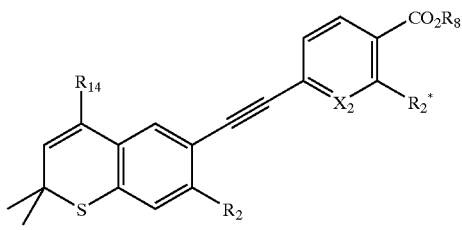

where $X_2$ is CH or N, and;

$R_2$ is H, F, or $OCH_3$, and;

$R_2^*$H or F, and;

$R_8$ is H, or lower alkyl of 1 to 6 carbons, and;

$R_{14}$ is selected from the group consisting of phenyl, 4-(lower-alkyl)phenyl, 5-(lower alkyl)-2-thienyl, and 6-(lower alkyl)-3-pyridyl where lower alkyl has 1 to 6 carbons, or a pharmaceutically acceptable salt of said compound.

Another class of compounds for use in a preferred embodiment of the present invention has the following structure:

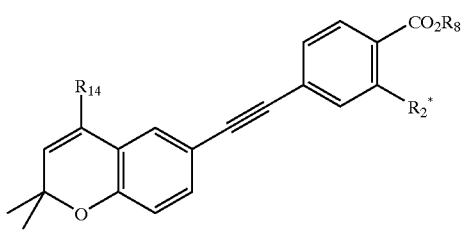

where $R_2^*$ is H or F;

$R_8$ is H, or lower alkyl of 1 to 6 carbons, and $R_{14}$ is selected from the group consisting of phenyl, and 4-(lower-alkyl)phenyl, where lower alkyl has 1 to 6 carbons, or a pharmaceutically acceptable salt of said compound.

Another preferred compound class has the following structure:

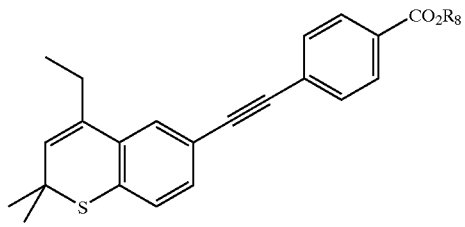

where $R_8$ is H, lower alkyl of 1 to 6 carbons, or a pharmaceutically acceptable salt of said compound.

Yet another preferred compound is one having the following structure:

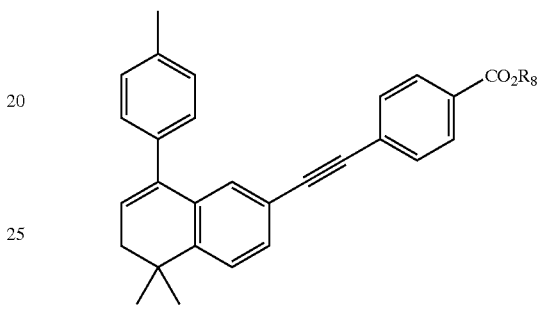

where $R_8$ is H, lower alkyl of 1 to 6 carbons, or a pharmaceutically acceptable salt of said compound. When $R_8$ is H, this compound is termed AGN 193109.

Yet another class of compounds contemplated for use in the present invention is that having the structure:

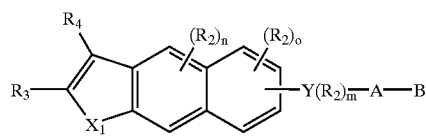

wherein $X_1$ is: $-C(R_1)_2-$, $-C(R_1)_2-C(R_1)_2-$, $-S-$, $-O-$, $-NR_1-$, $-C(R_1)_2-O-$, $-C(R_1)_2-S-$, or $C(R_1)_2-NR_1-$; and $R_1$ is independently H or alkyl of 1 to 6 carbons; and $R_2$ is optional and is defined as lower alkyl of 1 to 6 carbons, F, Cl, Br, I, $CF_3$, fluoro substituted alkyl of 1 to 6 carbons, OH SH, alkoxy of 1 to 6 carbons, or alklthio of 1 to 6 carbons; and m is an integer between, and including, 0 and 4; and n is an integer between, and including, 0 and 2; and o is an integer between, and including, 0 and 3; and $R_3$ is H, lower alkyl of 1 to 6 carbons, F, Cl, Br or I; and $R_4$ is $(R_5)_p$-phenyl, $(R_5)_p$-naphthyl, $(R_5)_p$-heteroaryl where the heteroaryl group is five-membered or 6-membered and has 1 to 3 heteroatoms selected from the group consisting of O, S, and N; and p is an integer between, and including, 0 and 5; and $R_5$ is optional and is defined as independently F, Cl, Br, I, $NO_2$, $N(R_8)_2$, $N(R_8)COR_8$, $N(R_8)CON(R_8)_2$, OH, $OCOR_8$, $OR_8$, CN, COOH, $COOR_8$, an alkyl group having from 1 to 10 carbons, an alkenyl group having from 1 to 10 carbons and 1 to three double bonds, alkynyl group having from 1 to 10 carbons and 1 to 3 triple bonds, or a (trialkyl)silyl or (trialkyl)silyloxy group where the alkyl groups independently have from 1 to 6 carbons; and Y is a phenyl or naphthyl group, or a heteroaryl selected from the group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or Y is $-(CR_3=CR_3)_r-$; and r is an integer between, and including, 1 and 3; and A is $(CH_2)_q$ where q is an integer from 0–5, lower branched chain alkyl having from 3 to 6 carbons, cycloalkyl having from 3 to 6 carbons, alkenyl having from 2 to 6 carbons and 1 or 2 double bonds, alkenyl having from 2 to 6 carbons and 1 or 2 triple bonds, with the proviso that when Y is $-(CR_3=CR_3)_r-$ then A is $(CH_2)_q$ and q is 0; and B is H, COOH or a pharmaceutically acceptable salt thereof, $COOR_8$, $CONR_9R_{10}$, $-CH_2OH$, $CH_2OR_{11}$, CHO, $CH(OR_{12})_2$, $CHOR_{13}O$, $-COR_7$, $CR_7(OR_{12})_2$, $CR_7OR_{13}O$, or $Si(C_{1-6alkyl})_3$, wherein $R_7$ is an alkyl, cycloalkyl or alkenyl group containing 1 to 5 carbons, $R_8$ is an alkyl group of 1 to 10 carbons or (trimethylsilyl)alkyl, where the alkyl groups has 1 to 10 carbons, or a cycloalkyl group of 5 to 10 carbons, or $R_8$ is phenyl or lower alkylphenyl, $R_9$ and $R_{10}$ independently are H, a lower alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is a divalent alkyl radical of 2–5 carbons. A non-exclusive list of compounds falling within this description, and methods for making this class of compounds are disclosed in U.S. Pat. No. 5,728,846 to Vuligonda et al., the disclosure of which is hereby incorporated by reference as part of this application.

Also useful in the present invention are compounds of the formula:

$$Y_3(R_4)-X-Y_1(R_1R_2)-Z-Y_2(R_2)-A-B$$

Where $Y_1$ is phenyl, naphthyl, or heteroaryl selected from the group consisting of pyridyl, thienyl, furyl, pyridazinyl, pyrimidinyl, pyrazinyl, thiazonyl, ozazolyl, imidazolyl, and pyrrazolyl, said phenyl, naphthyl, and heteroaryl groups being substituted with an $R_1$ group, and further substituted or unsubstituted with one or two $R_2$ groups;

$R_1$ is $C_{1-10}$ alkyl, 1-ademantyl, 2-tetrahydropyranoxy, trialkylsilanyloxy where alkyl has up to 6 carbons, OH, alkoxy where the alkyl group has up to 10 carbons, alkylthio where the alkyl group has up to 10 carbons, or $OCH_2OC_{1-6}$ alkyl;

$R_2$ is lower alkyl of 1 to 6 carbons, F, Cl, Br, I, $CF_3$, $CF_2CF_3$, OH, $OR_3$, $NO_2$, $N(R_3)_2$, CN, $N_3$, $COR_3$, $NHCOR_3$, COOH, or $COOR_3$;

X is $(C(R_3)_2$, S, SO, $SO_2$, O or $NR_3$;

Z is

—C≡C—,
—N=N—,
—N(O)=N—,
—N=N(O)—,
—N=CR_3—,
—CR_3=N,
—(CR_3=CR_3)_n— where n is an integer having the value 0–5,
—CO—NR_3—,
—CS—NR_3—,
—NR_3—CO,
—NR_3—CS,
—COO—,
—OCO—;
—CSO—;
—OCS—; or
—CO—CR_3=R_3—O, $R_3$ is independently H or lower alkyl of 1 to 6 carbons;

$Y_2$ is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being unsubstituted or substituted with one or two $R_2$ groups, or when Z is $-(C_3=CR_3)_n-$ and n is 3, 4 or 5 then $Y_2$ represents a direct valence bond between said $-(CF_3=CR_3)_n$ group and B;

$Y_3$ is phenyl, naphthyl, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being unsubstituted or substituted with one to three $R_4$ groups, where $R_4$ is alkyl of 1 to 10 carbons, fluoro-substituted alkyl of 1 to 10 carbons, alkenyl of 2 to 10 carbons and having 1 to 3 triple bonds, F, Cl, Br, I, $NO_2$, CN, $NR_3$, $N_3$, COOH, $COOC_{1-6}$ alkyl, OH, SH, $OC_{1-6}$ alkyl, and $SC_{1-6}$ alkyl;

A is $(CH_2)_q$ where q is from 0–5, lower branched alkyl having 3–6 carbons, cycloalkyl having 3–6 carbons, alkenyl, having 2–6 carbons and 1–2 double bonds, alkynyl having 2–6 carbons and 1 to 2 triple bonds, and B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_{13}O$, or $Si(C_{1-6}alkyl)_3$, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound. These compounds are disclosed in U.S. patent application Ser. No. 08/840,040, to Song et al., which application shares common ownership with the present application and is incorporated by reference herein in its entirety.

Additional RAR antagonists or inverse agonists are described in U.S. patent application Ser. No. 08/845,019, to Song and Chandraratna, which is incorporated by reference herein in its entirety; this application shares common ownership with the present application. Also, compounds useful in the methods of the present invention are disclosed in International Application Publication No. WO 94/14777, to Yoshimura et al., which is also incorporated by reference herein in its entirety. This latter application discloses RAR antagonists. A non-exclusive list of the structures of some preferred compounds disclosed therein can be found in FIG. 1 hereof.

Furthermore, the structures of additional compounds useful in the present invention are disclosed below.

A.

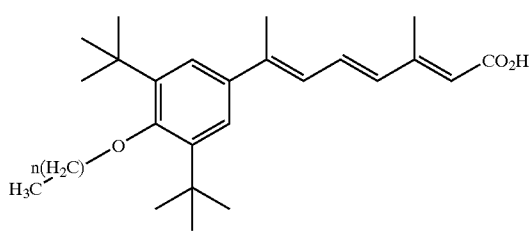

where n is an integer from 1 to 10.

B.

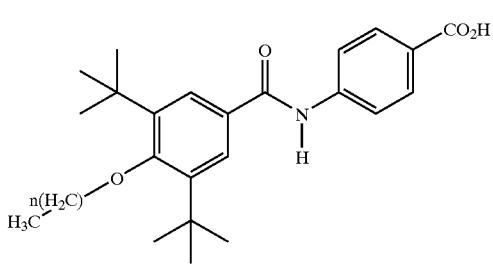

where n is an integer from 1 to 10.

C.

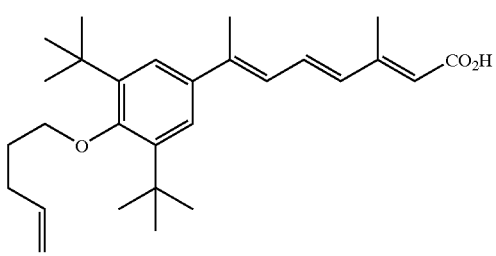

D.

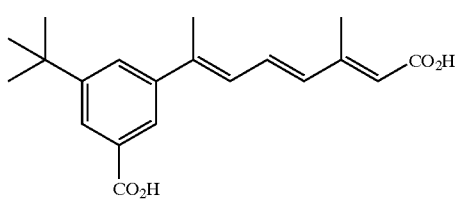

E.

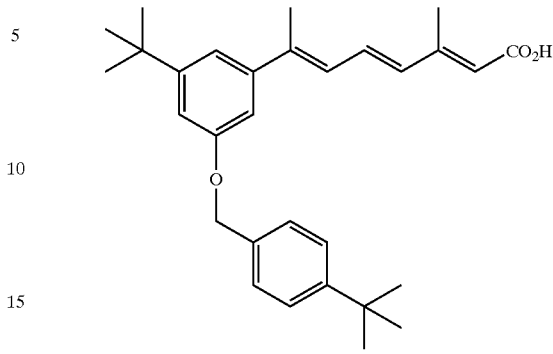

A particularly preferred subgroup of RAR antagonists or inverse agonists is the set of those RAR antagonists or inverse agonists that lack antagonist or inverse agonist activity at one or more subclass of RARs, such as the RARα, RARβ, or RARγ receptors; such "subclass-specific" activity may result in the minimization of toxicity of the drug. Such compounds may have activity only at the RARα, RARβ, or RARγ receptors, or at any combination of these (other than at all of them). Determination of whether a compound has subclass-specific specific inverse agonist activity is done through translational screening as disclosed in U.S. patent application Ser. No. 09/042,943, to Klein et al., and Ser. No. 09/108,298, to Nagpal et al., both of which are incorporated by reference herein in their entirety.

The compounds disclosed herein clearly suggest the synthesis and use of other compounds structurally similar to these, for use in the methods of the present invention. In addition to the compounds referred to herein, other agents that have RAR antagonist and/or inverse agonist activity are also anticipated to arrest spermatogenesis in mammals and thus be useful as male contraceptive agents in the invention of the present application.

The effective agents of the present invention may be provided orally, as in a liquid, syrup, suspension, tablet, capsule, gelatin-coated formulation or the like. Additionally, the contraceptive agents of the present invention have been demonstrated to be effective when applied topically. Topical delivery means include creams, gels, lotions, emulsions, suspensions, skin patches and the like. Additional delivery means may include inhalants, suppositories, and nasal sprays. Time-release formulations may be made for either oral or topical delivery.

For therapeutic applications in accordance with the present invention the antagonist compounds are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For example, preparation of topical formulations are well described in Remington's Pharmaceutical Science, Edition 17, Mack Publishing Company, Easton, Pa.; incorporated by reference herein. For topical application, the RAR antagonist or inverse agonist compounds could also be administered as a powder or spray, particularly in aerosol form. If the drug is to be administered systemically, it may be prepared as a powder, pill, tablet or the like or as a syrup or elixir suitable for oral administration. For intravenous or intraperitoneal administration, the drug compound will be prepared as a solution or suspension capable of being administered by injection. In certain cases, it may be useful to formulate the antagonist compounds by injection. In certain cases, it may be useful to formulate the antagonist compounds in suppository form or as extended release formulation for deposit under the skin or intramuscular injection.

The antagonist or inverse agonist compounds will be administered in a therapeutically effective dose in accordance with the invention. A therapeutic concentration will be that concentration which is effective to cause diminution or cessation of spermatogenesis in the testes of the male mammal. It is currently thought that a formulation containing between about 0.5 and about 0.001 mg/kg of body weight, more preferably between about 0.3 mg/kg and 0.005 mg/kg, even more preferably about 0.075 mg/kg of body weight and about 0.01 mg/kg of body weight will constitute a therapeutically effective concentration for oral application, with routine experimentation providing adjustments to these concentrations for other routes of administration if necessary.

Accordingly, in one embodiment the present invention comprises a method of inhibiting spermatogenesis in a mammal comprising the administration of an effective amount of an RAR antagonist or RAR inverse agonist at time intervals sufficient to inhibit or arrest spermatogenesis. In a further embodiment, the mammal is a human.

In a further preferred embodiment, the RAR antagonist or RAR inverse agonist is administered orally through the use of a liquid, syrup, suspension, tablet, capsule, or gelatin-coated formulation. In another preferred embodiment, the RAR antagonist or RAR inverse agonist is topically administered, through the use of means including a patch, cream, lotion, emulsion, or gel. In yet another embodiment, the RAR antagonist or RAR inverse agonist is formulated in an inhalant, suppository or nasal spray.

DETAILED DESCRIPTION OF THE INVENTION

The present invention concerns compositions and methods for the prophylactic prevention of pregnancy by the inhibition or arrest of spermatogenesis in male mammals. Spermatogenesis occurs in the seminiferous tubules of the testes of sexually mature male mammals. These tubules consist of a basement membrane surrounding an intra-tubule lumen. Specialized columnar cells termed Sertoli cells lie against the basement membrane and protrude into the lumen; the germ cells remain closely associated with the Sertoli cells throughout spermatogenesis.

Spermatogonia, male gamete stem cells, lie between the Sertoli cells and the basement membrane. Mitosis of a spermatogonium gives rise to two daughter cells; one may remain near the basement membrane as a spermatogonium and the other may develop, through subsequent rounds of mitosis, into a primary spermatocyte. As it develops the cells that become diploid primary spermatocytes are crowded closer to the tubule lumen.

The primary spermatocyte then enters meiosis and gives rise to haploid spermatids. These spermatids remain closely associated with the Sertoli cell, now at a location close to the lumen, and undergo a metamorphosis mediated partly by the Sertoli cell, maturing into spermatozoa. These cells are then released into the lumen of the seminiferous tubule.

The seminiferous tubules are closely packed together in the testes, being separated by connective tissue containing fibrocytes and vessels. An inhabitant of the spaces between the tubules is a steroidogenic somatic cell termed the Leydig cell. These cells synthesize the steroid hormone testosterone, which is an important stimulus for the differentiation of germ cells; the hormone diffuses into the seminiferous tubules where it stimulates spermatogenesis.

The time course of complete spermatogenesis is long; approximately 64 days in humans and 54 days in rats. This time course can be divided into 4 stages. In the first stage, spermatocytogenesis, the spermatogonia divide and give rise to primary spermatocytes. In the second stage, the primary spermatocytes undergo meosis and give rise to spermatids. In the third stage, spermoigenesis, the spermatids metamorphize into spermatozoa. In the final stage, maturation, the spermatozoa mature and are released into the seminiferous tubule. The spermatozoa undergo final maturation in the epiphysis. Cells in each of these four stages can be seen as "layers" in normal seminiferous tubules, with the least mature cells nearer the basement membrane, and the most mature cells near the lumen. The absence of cells of one or more stage is indicative of an event blocking or arresting a stage in spermatogenesis.

Although the exact mechanism underlying hormonal and gene regulation occurring in spermnatogenesis is not precisely known, and the scope of the present invention is not to be limited by theory, it is believed that testosterone production is regulated by the pituitary hormone, luteinizing hormone (LH). Another pituitary hormone, follicle-stimulating hormone (FSH), is also involved in the regulation of spermatogenesis, with primary hormone receptors being present on-the Sertoli cells. One effect of FSH on Sertoli cells is to stimulate the production of androgen-binding protein (ABP), which has a high binding affinity for testosterone and helps retain the steroid within the seminiferous tubules and sustain its effect on spermatogenesis.

Another peptide, termed inhibin, is thought to be secreted by Sertoli cells in response to the binding of FSH. Inhibin, in turn, appears to act on target cells within the pituitary to inhibit FSH secretion. Thus, inhibin may operate to act as a negative feedback regulator for the release of FSH and thus the production of ABP, with one consequence being the prevention of overstimulation by testosterone. Overproduction of inhibin could serve to lower the concentration of testosterone within the seminiferous tubules.

Thus, the regulation of spermatogenesis appears to include the regulation of gene expression and synthesis of a number of factors that either act as peptide hormones themselves or are involved in the sequestration or regulation of hormones important in spermatogenesis. Retinoid nuclear receptors (retinoic acid receptors (RAR) and retinoid X receptors (RXR)) are known to be involved in the ligand-mediated transcriptional regulation of various genes, which may include some of these factors.

The following examples are intended to illustrate further embodiments of the present invention and do not limit the scope of the invention, which is defined solely by the claims concluding this specification.

EXAMPLE 1

Oral Treatment of Spague-Dawley Rats with AGN 194310

Ninety-eight male and ninety-eight female Sprague-Dawley (Crl:CD®(SD) IGS BR) Charles River, Hollister, Calif. 95023) rats, approximately 8 to 10 weeks old, were used for the study. The rats were divided into the following groups: non-treated control, vehicle control, 0.005 mg/kg/day, 0.015 mg/kg/day and 0.15 mg/kg/day AGN 194310. AGN 194310 has the following chemical structure:

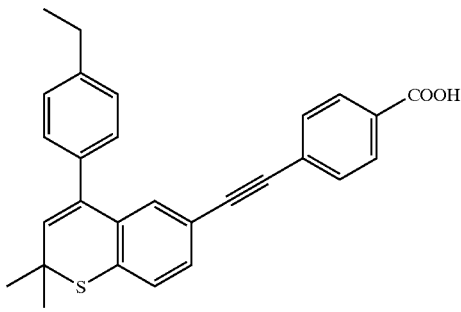

This compound, 4-[[4-(4ethylphenyl)-2,2-dimethyl-(2H)-thiochromen-6-yl]-ethynyl]-benzoic acid, may be synthesized using conventional organic synthetic means. The following reaction scheme is Applicants' currently preferred method of making this compound.

Step 1: A heavy-walled screw cap tube was charged with 3-methyl-2-butenoic acid (13.86 g, 138.4 mmol), 4-methoxy thiophenol (20.0 g, 138.4 mmol), and piperidine (3.45 g, 41.6 mmol). This mixture was heated to 105° C. for 32 hours, cooled to room temperature and dissolved in EtOAc (700 mL). The resulting solution was washed with 1M aqueous HCl, H$_2$O, and saturated aqueous NaCl before being dried over Na$_2$SO$_4$. Concentration of the dry solution under reduced pressure afforded an oil which upon standing in the freezer provided a crystalline solid. 3-(4-methoxyphenylsulfanyl)-3-methyl-butyric acid was isolated as pale-yellow crystals by washing the crystalline solid with pentane. (27.33 g, 82%). $^1$H NMR (300 MHz, CDCl$_3$) δ: 7.48 (2H, d, J=9.0 Hz), 6.89 (2H, d, J=8.9 Hz), 3.83 (3H, s), 2.54 (2H, s), 1.40 (6H, s).

Step 2: To a solution of 3-(4-methoxy-phenylsulfanyl)-3-methyl-butyric acid (20.0 g, 83.2 mmol) in 250 mL of benzene at room temperature was added a solution of oxalyl chloride (15.84 g, 124.8 mmol) in 10 mL of benzene over 30 minutes. After 4 hours the solution was washed with ice cold 5% aqueous NaOH (CAUTION: a large volume of gas is released during this procedure), followed by ice cold H$_2$O, and finally saturated aqueous NaCl. The solution was dried (Na$_2$SO$_4$) and concentrated under reduced pressure to give a clear yellow oil. This material was used without further purification in the next step. $^1$H NMR (300 MHz, CDCl$_3$) δ: 7.45 (2H, d, J=8.8 Hz), 6.90 (2H, d, J=8.8 Hz), 3.84 (3H, s), 3.12 (2H, s), 1.41 (6H, s). Step 3: To a solution of the acyl chloride product of Step 2 (21.5 g, 83.2 mmol) in 250 mL of CH$_2$Cl$_2$ at 0° C. was added dropwise a solution of SnCl$_4$ (21.7 g, 83.2 mmol) in 30 mL of CH$_2$Cl$_2$. After 2 hours the reaction was quenched by slow addition of 150 mL H$_2$O. The organic layer was washed with 1M aqueous HCl, 5% aqueous NaOH, H$_2$O, and finally saturated aqueous NaCl before being dried over MgSO$_4$. Concentration under reduced pressure and vacuum distillation of the residual oil (Bulb-to-bulb, 125–135° C., 5 mm/Hg) afforded 14.48 g (78%) of 6-methoxy-2,2-dimethyl-thiochroman4-one as a pale-yellow oil. $^1$H NMR (300 MHz, CDCl$_3$) δ: 7.62 (1H, d, J=2.9 Hz), 7.14 (1H, d, J=8.6 Hz), 7.03 (1H, dd, J=2.8 Hz), 3.83 (3H, s), 2.87 (2H, s), 1.46 (6H, s).

Step 4: To a solution of 6-methoxy-2,2-dimethyl-thiochroman-4-one (6.0 g, 27 mmol) in 50 mL CH$_2$Cl$_2$ cooled to −23° C. was added BBr$_3$ (20.0 g, 80.0 mmol; 80.0 mL of a 1M solution in CH$_2$Cl$_2$) over a 20 minute period. After stirring for 5 hours at −23° C. the solution was cooled to −78° C. and quenched by the slow addition of 50 mL of H$_2$O. Upon warming to room temperature the aqueous layer was extracted with CH$_2$Cl$_2$ and the combined organic layers were washed with saturated aqueous NaHCO$_3$, H$_2$O, and saturated aqueous NaCl before being dried over MgSO$_4$. Removal of the solvents under reduced pressure gave a green-brown solid which upon recrystalization (Et$_2$O/hexanes) afforded 2.25 g (40%) of 6-hydroxy-2,2-dimethylthiochroman-4-one as a light brown solid. $^1$H NMR (300 MHz, CDCl$_3$) δ:7.63 (1H, d, J=2.8 Hz), 7.15 (1H, d, J=8.5 Hz), 7.01 (1H, dd, J=2.8, 8.5 Hz), 2.87 (2H, s), 1.46 (6H, s).

Step 5: To a solution of 6-hydroxy-2,2-dimethylthiochroman-4-one (165.0 mg, 0.79 mmol) in 5.0 mL of anhydrous pyridine at 0° C. was added trifluoromethanesulfonic anhydride (245.0 mg, 0.87 mmol). After 4 hours at 0° C. the solution was concentrated and the residual oil dissolved in Et$_2$O, washed with H$_2$O followed by saturated aqueous NaCl, and dried over MgSO$_4$. Removal of the solvents under reduced pressure and column chromatography (5% EtOAc/hexanes) afforded 126.0 mg (47%) of 2,2-Dimethyl-4-oxo-thiochroman-6-yl trifluoromethanesulfonate as a colorless solid. $^1$H NMR (300 MHz, CDCl$_3$) δ: 7.97 (1H, s), 7.32 (2H, s), 2.90 (2H, s), 1.49 (6H, s).

Step 6: A solution of 2,2-dimethyl4-oxo-thiochroman-6-yl trifluoromethanesulfonate (2.88 g, 8.50 mmol) in 10 mL Et$_3$N and 20.0 mL DMF was sparged with argon for 10 minutes. To this solution was added trimethylsilylacetylene (4.15 g, 42.0 mmol) and bis(triphenylphosphine)-palladium (II) chloride (298.0 mg, 0.425 mmol). The solution was heated to 95° C. for 5 hours, cooled to room temperature, and diluted with H$_2$O. Extraction with EtOAc was followed by washing the combined organic layers with H$_2$O and saturated aqueous NaCl and drying over MgSO$_4$. Concentration of the dry solution under reduced pressure and isolation of the product by column chromatography (3% EtOAc/hexanes) afforded 2.23 g (91%) of the 2,2-dimethyl-6-trimethylsilanylethynyl-thiochroman-4-one as an orange oil. $^1$H NMR (300 MHz, CDCl$_3$) δ: 8.18 (1H, d, J=1.9 Hz), 7.34 (1H, dd, J=1.9, 8.1 Hz), 7.15 (1H, d, J=8.1 Hz), 2.85 (2H, s), 1.45 (6H, s), 0.23 (9H, s).

Step 7: A solution of 2,2-dimethyl-6-trimethylsilanylethynyl-thiochroman-4-one (110.0 mg, 0.38 mmol) and K$_2$CO$_3$ (40.0 mg, 0.29 mmol) in 10.0 mL MeOH was stirred overnight at room temperature. The solution was diluted with H$_2$O and extracted with Et$_2$O. The combined organic layers were washed with H$_2$O and saturated aqueous NaCl and dried over MgSO$_4$. Removal of the solvent under reduced pressure afforded 81 mg (99%) of the 6-ethynyl-2,2-dimethylthiochroman-4-one as an orange oil. $^1$H NMR (300 MHz, CDCl$_3$) δ:8.20 (1H, d, J=1.9Hz), 7.46(1H, dd, J=1.9, 8.1 Hz), 7.18 (1H, d, J=8.1 Hz), 3.08 (1H, s), 2.86 (2H, s), 1.46 (6H, s).

Step 8: A solution of 6-ethynyl-2,2-dimethylthiochroman-4-one (82.0 mg, 0.38 mmol) and ethyl 4-iodobenzoate (104.9 mg, 0.38 nmuol) in 5.0 mL Et$_3$N was purged with argon for 10 minutes. To this solution were added bis(triphenylphosphine)-palladium(II) chloride (88.0 mg, 0.12 mmol) and copper(I) iodide (22.9 mg, 0.12 mmol). After sparging for an additional 5 minutes with argon, the solution was stirred overnight at room temperature. The reaction mixture was filtered through a pad of Celite using an Et$_2$O wash. Concentration of the filtrate under reduced pressure, followed by column chromatography of the residual solid, afforded 100 mg (72%) of ethyl 4-[(2,2-dimethyl-4-oxo-thiochroman-6-yl)ethynyl]-benzoate as a yellow solid. $^1$H NMR (300 MHz, CDCl$_3$) δ: 8.25 (1H, d, J=1.8 Hz), 8.00 (2H, d, J=8.4 Hz), 7.55 (2H, d, J=8.4 Hz), 7.53 (1H, dd, J=1.8, 8.2 Hz), 7.21 (1H, d, J=8.2 Hz), 4.37 (2H, q, J=7.1 Hz), 2.88 (2H, s), 1.47 (6H, s), 1.39 (3H, t, J=7.1 Hz).

Step 9: A solution of sodium bis(trimethylsilyl)amide (1.12 g, 6.13 mmol) in 16.2 mL of THF was cooled to −78° C. and a solution of ethyl 4-(2,2-dimethyl-4-oxo-thiochroman-6-ylethynyl)-benzoate (1.86g, 5.10 mmol) in 15.0 mL was added slowly. After 30 minutes a solution of 2-[N,N-bis(trifluoromethanesulfonyl)amino]-5-pyridine (2.40 g, 6.13 mmol) in 10 mL of THF was added. After 5 minutes the solution was warmed to room temperature and stirred overnight. The reaction was quenched by the addition of saturated aqueous $NH_4Cl$ and extracted with EtOAc. The combined organic layers were washed with 5% aqueous NaOH and $H_2O$ before being dried ($MgSO_4$) and concentrated under reduced pressure. Ethyl 4-((2,2-dimethyl4-trifluoromethanesulfonyloxy-(2H)-thiochromen-6-yl) ethynyl)-benzoate, 1.53 g (61%), was isolated by column chromatography (2% EtOAc/hexanes) as a yellow solid. $^1H$ NMR (300 MHz, $CDCl_3$) δ: 8.03 (2H, d, J=8.4 Hz), 7.61 (1H, d, J=1.8 Hz), 7.59 (2H, d, J=8.4 Hz), 7.41 (1H, dd, J=1.8, 8.1 Hz), 7.29 (1H, d, J=8.1 Hz), 5.91 (1H, s), 4.39 (2H, q, J=7.1 Hz), 1.53 (6H, s), 1.41 (3H, t, J=7.1 Hz).

Step 10: A solution of 4-ethylbromobenzene (670.9 mg, 3.63 mmol) in 4.0 mL of THF was cooled to −78° C. and tert-butyllithium (464.5 mg, 7.25 mmol, 4.26 mL of a 1.7M solution in pentane) was added to give a yellow solution. After 30 minutes a solution of $ZnCl_2$ (658.7 mg, 4.83 mmol) in 8.0 mL THF was slowly added via cannula. The resulting solution was warmed to room temperature and transferred via cannula to a solution of ethyl 4-(2,2-dimethyl-4-trifluoromethanesulfonyloxy-(2H)-thiochromen-6-ylethynyl)-benzoate (1.20 g, 2.42 mmol) and tetrakis (triphenylphosphine)palladium(0) (111.7 mg, 0.097 mmol) in 8.0 mL THF. This solution was heated to 50° C. for 1 hour, cooled to room temperature, and the reaction quenched by the addition of saturated aqueous $NH_4Cl$. The solution was extracted with EtOAc and the combined organic layers were washed with $H_2O$ and saturated aqueous NaCl before being dried ($MgSO_4$) and concentrated under reduced pressure. Ethyl 4-[[4-(4-ethylphenyl)-2,2-dimethyl-(2H)-thiochromen-6-yl]-ethynyl]-benzoate was isolated by column chromatography (5% EtOAc/hexanes) as a colorless oil. $^1H$ NMR (300 MHz, $CDCl_3$) δ: 7.99 (2H, d, J=8.2 Hz), 7.52 (2H, d, J=8.4 Hz), 7.40 (5H, m), 7.35 (2H, m), 5.85 (1H, s), 4.38 (2H, q, J=7.1 Hz), 2.72 (2H, q, J=7.6 Hz), 1.48 (6H, s), 1.40 (3H, t, J=7.1 Hz), 1.30 (3H, t, J=7.6 Hz).

Step 11: To a solution of ethyl 4-[[4-(4-ethylphenyl)-2,2-dimethyl-(2H)-thiochromen-6-yl]-ethynyl]-benzoate (940.0 mg, 2.08 mmol) in 10.0 mL THF and 5.0 mL EtOH was added NaOH (416.0 mg, 10.4 mmol, 5.2 mL of a 2M aqueous solution). The resulting solution was stirred overnight at room temperature. The reaction mixture was acidified with 10% aqueous HCl and extracted with EtOAc. The combined organic layers were washed with $H_2O$, saturated aqueous NaCl, and dried ($Na_2SO_4$) before removing the solvent under reduced pressure. The residual solid was recrystallized from $CH_3CN$ to give 786.0 mg (89%) of 4-[[4-(4-ethylphenyl)-2,2-dimethyl-(2H)-thiochromen-6-yl]-ethynyl]-benzoic acid as a colorless solid. $^1H$ NMR (300 MHz, $d_6$-acetone) δ: 8.01 (2H, d, J=8.3 Hz), 7.60 (2H, d, J=8.5 Hz), 7.42 (2H, m), 7.29 (2H, m), 7.22 (3H, m), 5.94 (1H, s), 2.69 (2H, q, J=7.7 Hz), 1.47 (6H, s), 1.25 (3H, t, J=7.7 Hz). This compound, the final desired product, was termed AGN 194310.

The AGN 194310 compound was provided as follows: the compound was dissolved in capric/caprylic triglyceride (CCT) at a variety of doses, either 0.001% (v/v) AGN 194310, 0.003% (v/v) AGN 194310, or 0.01% (v/v) AGN 194310. Control animals received the CCT vehicle without the AGN 194310 active ingredient (AGN 194310 Vehicle). Although many retinoids and retinoid analogs are light labile, this compound is relatively stable to normal light.

Newly arrived animals were quarantined for at least 7 days prior to their use in the study. All animals used in the study appeared to be in good health, with no evidence of disease or physical abnormality.

One hundred ninety-six animals were distributed into thirteen groups as follows: Groups 1 through 5 were Main Study groups. Groups 6–9 were used for Toxicokinetic studies. Groups 10–13 were Main Study Recovery groups. The characteristics of each group are shown in Table 1 below.

TABLE 1

| Group No. | Number & Sex | Test Material | Total Daily Amount of AGN 194310 (mg/kg/day) | Total Daily Amount of Test Prep. (ml/kg/day) |
|---|---|---|---|---|
| 1 | 10M/10F | Non-Treated Control | N/A | N/A |
| 2 | 10M/10F | AGN 194310 Vehicle | N/A | 1.5 |
| 3 | 10M/10F | 0.001% AGN 194310 | 0.005 | 0.5 |
| 4 | 10M/10F | 0.003% AGN 194310 | 0.015 | 0.5 |
| 5 | 10M/10F | 0.01% AGN 194310 | 0.15 | 1.5 |
| 6 | 4M/4F | AGN 194310 Vehicle | N/A | 1.5 |
| 7 | 8M/8F | 0.001% AGN 194310 | 0.005 | 0.5 |
| 8 | 8M/8F | 0.003% AGN 194310 | 0.015 | 0.5 |
| 9 | 8M/8F | 0.01% AGN 194310 | 0.15 | 1.5 |
| 10 | 5M/5F | AGN 194310 Vehicle | N/A | 1.5 |
| 11 | 5M/5F | 0.001% AGN 194310 | 0.005 | 0.5 |
| 12 | 5M/SF | 0.003% AGN 194310 | 0.015 | 0.5 |
| 13 | 5M/5F | 0.01% AGN 194310 | 0.15 | 1.5 |

The drug was administered using a graduated syringe and a 20×3 inch animal feeding needle. Drug was given to each animal in a single dose per day. Animals were observed at lease once daily during the course of the study for mortality, general health, behavior and any apparent physical or pharmacological abnormalities.

Animals were weighed on the first day of the study and once per week thereafter, and the body weights recorded. The body weights were used for the dosage calculations. For all the Main Study and Recovery animals, food (Purina Certified Rodent Chow, meal form) was placed into tared glass jars and left in the animal cages. Jars were removed and weighed once weekly. Food was added to the jars when necessary. Food consumption was not recorded for the animals used in the toxicokinetic satellite studies.

Urine was collected from animals in the Main Study and Recovery groups during week 4 of the treatment period, and from Recovery group animals during week 4 of the recovery period. Urine was analyzed for: blood (hemoglobin and erythrocytes), bilirubin, color, glucose, ketones, leukocytes, microscopic evaluations of any urine sediment, nitrate, pH, protein, specific gravity, transparency, and urobilinogen.

Blood was collected from animals constituting the Main Study and Recovery groups at the end of the treatment and recovery periods, respectively. Before blood collection, the animals were allowed to fast for 16 hours, then blood was collected from each animal via cardiac puncture under anesthesia. The animals were sacrificed thereafter.

The following tests were performed using the blood samples collected: hematocrit (total blood cell volume), total hemoglobin, mean cell volume, mean corpuscular hemoglobin (MCH), mean corpuscular hemoglobin concentration (MCHC), platelet count, red blood cell count (RBC), total white blood cell count (WBC), and a differential WBC count for basophils, eosinophils, lymphocytes, monocytes, neutrophils.

The concentration of drug in the blood was determined from blood drawn from the retro-orbital sinus of the right eye on Day 7 of the study as follows: for rats in groups 7 through 9 (4/sex/group/timepoint, with each animal being bled no more than 3 times), blood (approximately 1 ml) was drawn prior to being given the drug, and at approximately 2, 6, 8, 12 and 24 hours post-dosing. The vehicle-treated rats (group 6) were bled at approximately 8 and 24 hours post-dosing. The rats in groups 6 through 9 were similarly bled on Day 22 of the study, then euthanized. All blood was drawn into tubes containing EDTA to prevent coagulation, and placed on ice prior to analysis. The blood was assayed for the presence of AGN 194310 by gas chromatography/mass spectrometry.

Animals were euthanized by inhalation of carbon dioxide. A complete necropsy was performed on all Main Study and Recovery group animals that died, or were euthanized due to moribund conditions, or were euthanized on scheduled sacrifice.

The following organs were weighed for necroscopized animals: adrenal glands, ovaries, kidneys, pituitary gland, liver, spleen, heart, testes, and brain. In the case of organ pairs, both organs were weighed together.

The following tissues and organs were isolated, trimmed if necessary, and preserved in 10% buffered formalin for histopathological evaluation: adrenal glands, mammary gland (with skin), aorta, ovaries, bone/bone marrow, pancreas, femur, pituitary gland, tibia, prostate gland, knee joint, salivary glands, parotid, brain, sub-maxillary, cervix sciatic nerve, diaphragm, seminal vesicle, epididymides, skeletal muscle (thigh), eyes, spinal chord (thoracic), spleen, esophagus, sternum, stomach, testes, duodenum, thymus, jejunum, thyroid gland with parathyroids, ileum, any tissues with lesion(s), cecum, tongue, colon, trachea, heart, bladder, kidneys, uterus, liver, ureter, lungs, urethra, lymph nodes (vaginal, cervical, mediastinal, mesenteric).

Target tissues and organs from the Vehicle (control) and high-dose groups were imbedded in paraffin, and tissue sections made. The sections were mounted and stained with hematoxylin and eosin using standard histological techniques; such histopathological evaluation was performed using techniques well known in the art.

After review and comparison of the histological findings obtained at the end of treatment period in the vehicle alone control group (group 2) and Main Study high dose (0.15 mg/kg/day) group (group 5), only those tissues determined to be affected by the drug at the high dose were evaluated in the Main Study intermediate (0.015 mg/kg/day) and low dose (0.005 mg/kg/day) groups (groups 3 and 4, respectively). Similarly, only when treatment-related histological effects were observed in a given tissue or dosage group of animals were the affected tissues and dosage groups evaluated in the Recovery group. In the Recovery dosage groups that were so evaluated, the selected tissues were prepared and evaluated as set forth above.

No treatment-related deaths of study animals occurred during the course of the study. There were no statistically significant treatment-related effects on body weight during the treatment or recovery periods. The mean body weights of all study group animals were comparable throughout the study period. Nor were there treatment-related effects on food consumption between animals of different groups.

There were no apparent treatment-related effects among animals of different groups in any urinalysis parameters at the end of the treatment period. By contrast, urinalysis of Recovery group animals at the end of the recovery period revealed no spermatozoa counts in the 0.15 mg/kg/day male rat urine samples. There were no other treatment-related effects in any other groups at the end of the recovery period.

AGN 194310 was systemically absorbed following oral administration to rats and approached the peak concentration in plasma (Cmax) at 2 or 6 hours post dosing (Tmax). A dose dependent increase in systemic exposure to AGN 194310 was observed across the concentrations of AGN 194310. Similar Cmax and $AUC_{0-24hr}$ values (Area Under the Curve from 0 to 24 hours after dosage; this measures the concentration of drug in the blood during this time period monitored) were observed when rat blood was tested between the two collection periods. Pharmacokinetic parameters are presented in the following table:

TABLE II

| Formulation (dosage) | | 0.001%<br>AGN 194310<br>(0.005<br>mg/kg/day) | 0.003%<br>AGN 194310<br>(0.015<br>mg/kg/day) | 0.01%<br>AGN 194310<br>(0.15<br>mg/kg/day) |
|---|---|---|---|---|
| $Cmax^a$ | Day $7^c$ | 1.83 ± 0.55 | 4.73 ± 1.2 | 43.1 ± 7.2 |
| (ng/ml) | Day $22^c$ | 1.97 ± 0.75 | 5.32 ± 1.56 | 42.4 ± 9.3 |
| Tmax | Day $7^c$ | 2 | 2 | 6 |
| (hr) | Day $22^c$ | 2 | 2 | 6 |
| $AUC_{24\,hr}$ | Day $7^c$ | 19.6 ± 1.1 | 57.6 ± 2.6 | 668 ± 24 |
| (ng · hr/ml)$^b$ | Day $22^c$ | 20.8 ± 1.1 | 63.6 ± 2.7 | 675 ± 25 |

$^a$Mean ± SD (N = 8/dose/time point).
$^b$Mean ± SEM (N = 8/dose/time point).
$^c$The day 7 data were not statistically different from the day 22 data.

There were no noticeable differences between study animals observed during the postmortem pathological examination at the end of the treatment period. At the end of the recovery period, postmortem examinations revealed an apparent reduction of testes size in all five male rats that had been treated with AGN 194310 at a dosage level of 0.15 mg/kg/day. This finding was supported by a reduction in testes weight in male rats give the high drug dose (0.15 mg/kg/day) at the end of the treatment and recovery periods. Male rats in the other dosage groups showed no statistically significant reduction of testes weight.

Histological examination of thin sections of the testes revealed that all (10/10) of the male rats given the high dose of AGN 194310 underwent spermatogenic arrest at the end of treatment. No such effect appeared in males given the intermediate (0.015 mg/kg/day) or low (0.005 mg/kg/day) dosages of the drug. The seminiferous tubules of the high dose males were lined with one to two layers of germinal cells, rather than the usual four or more layers seen in normal seminiferous tubules. This change reflects a complete block of spermatogenesis.

Leydig cells appeared unaffected, nor was any evidence of an atrophic change seen in the secondary sex glands, such as the seminal vesicles and prostate, of the high dose males. In other words, the drug appears to target the seminiferous epithelium. Changes in the testes were not readily evident, either through visual or microscopic inspection at the end of the treatment period.

The rats in the Recovery group were permitted approximately a one-month period without exposure to the drug. In the male rats of the Recovery group, testicular atrophy was evident and accompanied morphologically by continuing cessation of spermatogenesis, monitored according to the criteria and methods mentioned above. However, reversibility of such inhibition was also evident, as could be seen by a focal increase in germ cell layers in individual tubules. The extent of this recovery varied from animal to animal and within a single testicular section.

None of the high dose male rats, either in the Main Study Group or the Recovery group, displayed inflammation or damage to stromal or vascular elements of the testis. Physiological effects of drug treatment other than those associated with spermatogenic arrest were not observed. The epididymis of the high dose rats showed an increase in exfoliated cells at the end of treatment and the absence of stored epididymal sperm at the end of recovery; these changes are expected secondary effects of spermatogenic arrest.

As the total time course of spermatogenesis is approximately 54 days in rats, the time period required to observe reversibility of complete spermatogenic arrest would be at least this long. Also, this time period would be expected to be additionally lengthened, depending upon the time required for the drug to be clear from the subject's system. In a separate experiment 88% of the drug was shown to be excreted within 2 weeks following treatment. Thus, this experiment provides evidence of reinitiation of spermatogenesis in animals of the Recovery group.

Thus, this experiment shows that daily oral delivery of the RAR antagonist AGN 194310 is sufficient to cause spermatogenic arrest in mammals, and that the effects of spermatogenic arrest in treated animals are reversed following cessation of AGN 194310 treatment. Although the exact mechanism of inhibition is not known, and, while not wishing to be bound by theory, the Applicants believe that the drug appears especially to affect, either directly or indirectly, primary spermatocytes. Thus, germ cells that have differentiated beyond the primary spermatocyte stage when treatment with an RAR antagonist or inverse agonist is initiated will continue to mature and differentiate into spermatozoa, while spermatogonia do not appear to differentiate beyond the primary spermatocytes stage. Since the $2^{nd}$, $3^{rd}$, and $4^{th}$ stages of spermatogenesis occur over an extended period before the release of the spermatozoa into the epididymis, this is why spermatozoa were still seen in the urine of the Main Study male rats at the end of treatment (despite clear spermatogenic arrest being visible in the testes tissue sections), while the male rats of the Recovery group have no detected spermatozoa in their urine (despite clear indications of renewed spermatogenesis in the testes of these rats).

Thus, in this experiment daily oral dosage of an RAR antagonist (inverse agonist), AGN 194310, at 0.15 mg/kg/day was sufficient to cause reversible spermatogenic arrest. By presenting these data the Applicants are not indicating that the experiment demonstrates an optimal dose, delivery method, or frequency of treatment. However, this experiment clearly shows the unanticipated result that an RAR antagonist or inverse agonist may be used as an effective male contraceptive, as claimed.

EXAMPLE 2

Topical Treatment of Spague-Dawley Rats with AGN 194310

An experiment was conducted in a manner substantially similar to that described in Example 1, with the following differences. Twenty-nine male and twenty-nine female Sprague-Dawley rats, approximately 7 weeks old were used for the study. Five rats/sex/group were designated as Main Study animals: (vehicle control, 0.025 mg/kg/day AGN 194310, and 0.25 mg/kg/day AGN 194310), and 7/sex/group designated as toxicokinetic satellite animals (0.025 mg/kg/day AGN 194310 and 0.25 mg/kglday AGN 194310). No "vehicle alone" control group was made for the toxicokinetic satellite animals. In this study there was no Recovery group.

The animals' backs were maintained shaven during the course of the study for application of the topical cream. The animals were treated daily with a topical formulation containing either AGN 194310 vehicle cream alone, 0.01% (w/w) AGN 194310 in the same vehicle cream, or 0.1% (w/w) AGN 194310 in the same vehicle cream. The vehicle cream consisted of a mixture of the following ingredients:

| Benzyl Alcohol | 1% (w/w) |
| Medium Chain Triglycerides | 25% (w/w) |
| Carbomer 1342 | 0.2% (w/w) |
| Sorbitan Monooleate | 0.2% (w/w) |
| Carbomer 934P | 1% (w/w) |
| EDTA | 0.05% (w/w) |
| 5 N Sodium Hydroxide | 2.72 (w/w) |
| Water | q.s. to 100% (w/w) |

The following Table shows the experimental design:

TABLE 3

| Group No. | Number & Sex | Test Material | Total Daily Amount of AGN 194310 (mg/kg/day) | Total Daily Amount of Test Prep. (gm/kg/day) |
| --- | --- | --- | --- | --- |
| 1 | 5M/5F | Vehicle Cream | N/A | 0.25 |
| 2 | 5M/5F | 0.01% AGN 194310 | 0.025 | 0.25 |
| 3 | 5M/5F | 0.1% AGN 194310 | 0.25 | 0.25 |
| 4 | 7M/7F | 0.01% AGN 194310 | 0.025 | 0.25 |
| 5 | 7M/7F | 0.1% AGN 194310 | 0.25 | 0.25 |

Daily dosages were calculated using the most recently obtained body weight, as shown below. The test or control creams were applied for 28 consecutive days to the shaved back of each animal in an area approximately equal to 35.5 $cm^2$. Application was made using a repeat pipettor, and the drug gently massaged into the skin. An Elizabethan collar was affixed around each animal's neck for a period of about 6 hours following treatment to prevent removal or systemic ingestion of the drug.

Blood was drawn at day 29 via cardiac puncture, as described in Example 1. The animals were first permitted to fast for approximately 16 hours prior to blood collection. Satellite animals were sacrificed on day 28.

Topical skin application of AGN 194310 did not result in any evidence of treatment-related skin irritation. No treatment-related clinical observations, differences in body weight, differences in food consumption, or in gross pathology were observed.

Male rats in all groups displayed no statistically significant hematological differences versus the control rats. However, there is a dose-dependent reduction in triglycerides in the male rats given the drug. Histopathological analysis reveals atrophy of the seminiferous tubules, with concomitant spermatogenic arrest in 0 out of 5 male rats in the 0.025 mg/kg/day group and 5 out of 5 male rats in the 0.25 mg/kg/day; spermatogenic arrest was detected as described in Example 1. Additionally, there was a notable reduction of germ cells in the head of the epididymis in the majority of males displaying spermatogenic arrest.

EXAMPLE 3

Reversibility of Spermatogenic Arrest

This experiment was conducted in a manner substantially similar to that of Example 1. Groups of male Sprague Dawley rats were treated orally for 4 weeks with either 0, 0.075, or 0.150 mg/kg/day of AGN 194310. Three to six animals from each group were sacrificed after 2 weeks of treatment, 6 animals from each group were sacrificed following 4 weeks of treatment and 6 animals from each group were sacrificed after 18–23 weeks of subsequent recovery after cessation of treatment. Histological and pathological examinations were done of the sacrificed animals, as in Example 1. Additionally, the animals in the 23 week recovery group were mated to normal, untreated female Sprague Dawley rats before being sacrificed to assess the reproductive function.

As in the previous examples, the control group of rats (no drug) displayed no abnormal histological or biochemical differences during the time course of the experiment, except for a single individual, which was found to have bilateral severe sperm granulomas due to segmental aplasia of the epididymides (a congenital defect).

All rats treated with 0.075 mg/kg of AGN 194310 displayed evidence of spermatogenic arrest after 2 and 4 weeks of treatment. No increase of round spermatidis were seen in the epididymal caput and cauda of these animals. The weight of the testes and epididymides of the treated animals was significantly reduced after 4 weeks of treatment, and this weight decrease persisted to some degree in rats sacrificed after 18 weeks of recovery. Histological analysis revealed that active spermatogenesis had resumed in the treated animals, but no mature sperm were seen in the epididymides.

After 23 weeks of recovery, 2 of the 3 rats had completely recovered with normal testes weights, a complete spermatogenesis cycle, and mature sperm in the epididymides. The remaining animals had complete spermatogenesis in the left testis, incomplete spermatogenesis in the right testis, and mature sperm in both epididymides. Interestingly, the seminal vesicles, of all the treated animals were normal; seminal vesicle weight is dependent on serum testosterone. These data suggest that serum testosterone function remains normal during treatment with AGN 194310. All tested animals were fertile after 23 weeks of recovery and able to reproduce healthy pups.

Among the animals treated with 0.150 mg/kg AGN 194310 similar results were seen. Spermatogenic arrest was observed in all rats treated after 2 and 4 weeks of treatment. After 23 weeks of recovery, 4 out of 6 rats appeared to have completely recovered, with active and complete spermatogenesis seen, and normal testes weight. These 4 rats were able to reproduce normally. The remaining two animals had incomplete spermatogenesis no mature sperm seen in the epididymides histologically.

These results indicate that the effects of the drug are fully reversible when administration of AGN 194310 is halted. Additionally, the results are expected to be substantially similar whether the drug is applied orally or topically.

EXAMPLE 4
Topical Administration of AGN 193109

This experiment is conducted as indicated in Example 2, except that the drug is 193109 rather than AGN 194310, and a Recovery group is monitored for a period of time post-treatment as in Example 3. Dosages of the '109 drug is the same as for the topical treatment with the '310 drug.

The results are substantially similar to those reported in Example 3 for AGN 194310. At the effective dose, spermatogenic arrest can be seen within thirty days after initiation of treatment by examination of the testes of the treated animals. A histological analysis of the testes reveals the absence of primary spermatocytes, spermatids and spermatozoa in the majority of animals' seminiferous tubules. These effects are reversible; a similar analysis conducted on the testes of males rats 12 weeks after administration demonstrates the repopulation of the tubules with males gametes in various stages of development.

In a preliminary test using a small population (5) male cynomologus monkeys, treatment with AGN 194310 at a daily dosage of 1.25 mg/kg did not result in inhibition or arrest of spermatogenesis. Those of skill in the art will recognize that these are initial results. Assuming arguendo these results are reproducible the results could be due to many factors, including, without limitation, suboptimal dosage, delivery vehicles or modes of treatment that are differentially effective in cynomologus monkeys and rats, or the possibility that AGN 194310 has different effects in monkeys as compared to rats. Those of skill in the art will also recognize that both rats and monkeys are commonly used and accepted animal models for drug efficacy in humans.

In light of the disclosure of this patent specification, the person of ordinary skill in the art would expect that treatment of a male human with an effective dosage of a RAR antagonist or inverse agonist able to inhibit spermatogenesis in male non-human mammals such as rats and/or monkeys, would have similar effects in humans, both in terms of spermatogenic arrest as well as reversibility. Depending upon the Kd of the antagonist or inverse agonist, such drugs may have to be given at dosage levels, or frequencies, other than those described above. By "Kd" is meant the binding constant; defined as that concentration of the drug at which 50% of the drug is bound to an RAR receptor. Additionally, the Applicants intend to make no statement herein that should be construed as a representation that the dosage levels and dosage frequencies mentioned herein are necessarily optimal.

It will be recognized by the person of ordinary skill in the art that the ability or failure of a given drug to stimulate a specific response, such as spermatogenic arrest, in one species or genus of male mammal is not necessarily indicative of the ability or failure of the same drug to stimulate the same response in another species or genus of mammals.

The invention is not to be seen as limited by the foregoing examples, which merely set forth certain preferred embodiments of the invention. Other embodiments can be found in the claims that conclude this specification.

What is claimed is:

1. A method for inhibiting the ability of a male mammal to conceive progeny, comprising: regularly administering to said male mammal an effective amount of an RAR antagonist or inverse agonist for a period of time effective to sufficiently reduce or eliminate spermatozoa in the semen of said male mammal.

2. The method of claim 1 wherein said RAR antagonist or inverse agonist has the chemical structure:

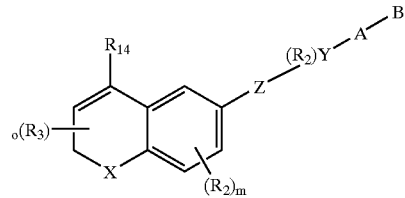

wherein
X is S, O, NR' where R' is H or alkyl of 1 to 6 carbons, or
X is $[C(R_1)_2]_n$ where $R_1$ is independently H or alkyl of 1 to 6 carbons, and n is an integer between, and including, 0 and 2, and;
$R_2$ is independently hydrogen, lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons, and;

$R_3$ is independently hydrogen, lower alkyl of 1 to 6 carbons or F, and;

m is an integer having the value of 0–3, and;

o is an integer having the value of 0–3, and;

Z is
- —C≡C—,
- —N=N—,
- —N=CR$_1$—,
- —CR$_1$=N,
- —(CR$_1$=CR$_1$)$_{n'}$— where n' is an integer having the value 0–5,
- —CO—NR$_1$—,
- —CS—NR$_1$—,
- —NR$_1$—CO,
- —NR$_1$—CS,
- —COO—,
- —OCO—;
- —CSO—;
- —OCS—;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R$_2$ groups, or when Z is —(CR$_1$=CR$_1$)$_{n'}$— and n' is 3, 4 or 5 then Y represents a direct valence bond between said (CR$_2$=CR$_2$)$_{n'}$ group and B;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COO$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, or tri-lower alkylsilyl, where R$_7$ is an alkyl, cycloalkyl or alkenyl group containing 1 to 5 carbons, R$_8$ is an alkyl group of 1 to 10 carbons or trimethylsilylalkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower akylphenyl, R$_{11}$ is lower alkyl, phenyl or lower alkylphenyl, R$_{12}$ is lower alkyl, and R$_{13}$ is divalent alkyl radical of 2–5 carbons, and R$_{14}$ is (R$_{15}$)$_r$-phenyl, (R$_{15}$)$_r$-naphthyl, or (R$_{15}$)$_r$-heteroaryl where the heteroaryl group has 1 to 3 heteroatoms selected from the group consisting of O, S and N, r is an integer having the values of 0–5, and R$_{15}$ is independently H, F, Cl, Br, I, NO$_2$, N(R$_8$)$_2$, N(R$_8$)COR$_8$, NR$_8$CON(R$_8$)$_2$, OH, OCOR$_8$, OR$_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons.

3. The method of claim 1 wherein said RAR antagonist or inverse agonist has the chemical structure:

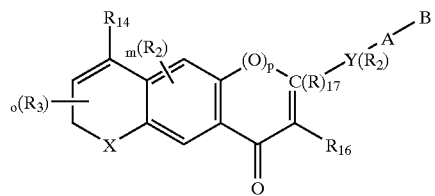

wherein

X is S, O, NR' where R' is H or alkyl of 1 to 6 carbons, or

X is [C(R$_1$)$_2$]$_n$ where R$_1$ is independently H or alkyl of 1 to 6 carbons, and n is an integer between, and including, 0 and 2, and;

R$_2$ is independently hydrogen, lower alkyl of 1 to 6 carbons, F, Cl, Br, I, CF$_3$, fluoro substituted alkyl of 1 to 6 carbons, OH, SH, alkoxy of 1 to 6 carbons, or alkylthio of 1 to 6 carbons, and;

R$_3$ is independently hydrogen, lower alkyl of 1 to 6 carbons or F, and;

m is an integer having the value of 0, 1, 2, or 3, and;

o is an integer having the value of 0, 1, 2, or 3, and;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R$_2$ groups, and;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds, and;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, or tri-lower alkylsilyl, where R$_7$ is an alkyl, cycloalkyl or alkenyl group containing 1 to 5 carbons, R$_8$ is an alkyl group of 1 to 10 carbons or trimethylsilylalkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons, and;

R$_{14}$ is (R$_{15}$)$_r$-Phenyl, (R$_{15}$)$_r$-naphthyl, or (R$_{15}$)$_r$-heteroaryl where the heteroaryl group has 1 to 3 heteroatoms selected from the group consisting of O, S and N, r is an integer having the values of 0, 1, 2, 3, 4 or 5, and;

R$_{15}$ is independently H, F, Cl, Br, I, NO$_2$, N(R$_8$)$_2$N(R$_8$) COR$_8$, NR$_8$CON(R$_8$)$_2$, OH, OCOR$_8$, OR$_8$, CN, an alkyl group having 1 to 10 carbons, fluoro substituted alkyl group having 1 to 10 carbons, an alkenyl group having 1 to 10 carbons and 1 to 3 double bonds, alkynyl group having 1 to 10 carbons and 1 to 3 triple bonds, or a trialkylsilyl or trialkylsilyloxy group where the alkyl groups independently have 1 to 6 carbons, and;

R$_{16}$ is H, lower alkyl of 1 to 6 carbons, and;

R$_{17}$ is H, lower alkyl of 1 to 6 carbons, OH or OCOR$_{11}$, and;

p is zero or 1, with the proviso that when p is 1 then there is no $R_{17}$ substituent group, and m is an integer between, and including, 0 and 2.

4. The method of claim 1 wherein said RAR antagonist or inverse agonist has the chemical structure:

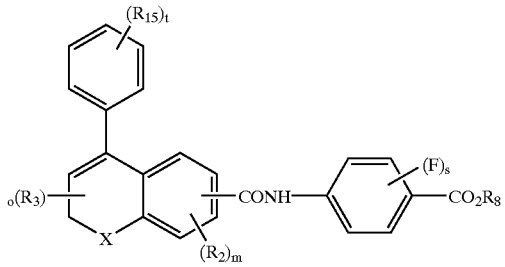

where

X is $C(R_1)_2$ or O, and;

$R_1$ is H or alkyl of 1 to 6 carbons, and;

$R_2$ is independently lower alkyl of 1 to 6 carbons, F, Cl, Br, I, $CF_3$, fluoro substituted alkyl of 1 to 6 carbons, OH, SH, alkoxy of 1 to 6 carbons, or alkylthio of 1 to 6 carbons, and;

m is an integer having the value of 0–3, and;

$R_3$ is independently lower alkyl of 1 to 6 carbons or F, and;

o is an integer having the value of 0–3, and;

s is an integer having the value of 1–3, and;

$R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, and;

$R_{15}$ is independently H, F, Cl, Br, I, $NO_2$, $N(R_8)_2$, $COR_8$, $NR_8CON(R_8)_2$, $OCOR_8$, $OR_8$, CN, an alkyl group having 1 to 10 carbons, fluoro substituted alkyl group having 1 to 10 carbons, an alkenyl group having 1 to 10 carbons and 1 to 3 double bonds, an alkynyl group having 1 to 10 carbons and 1 to 3 triple bonds, or a trialkylsilyl or trialkylsilyloxy group where the alkyl groups independently have 1 to 6 carbons, and;

t is an integer having the values of 0, 1, 2, 3, 4, or 5, and;

the CONH group is in the 6 or 7 position of the benzopyran, and in the 2 or 3 position of the dihydronaphthaline ring, or a pharmaceutically acceptable salt of said compound.

5. The method of claim 1 wherein said RAR antagonist or inverse agonist has the chemical structure:

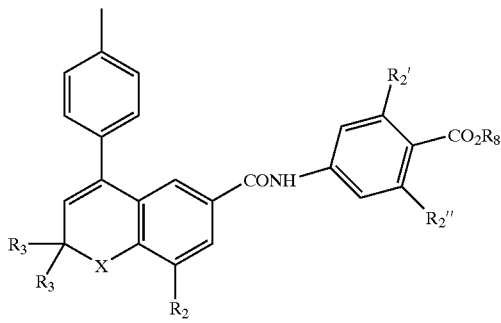

where

X is $C(CH_3)_2$ or O, and;

$R_2$ is H or Br, and;

$R_{2'}$ and $R_{2''}$ independently are H or F, and;

$R_3$ is H or $CH_3$, and;

$R_8$ is H, lower alkyl of 1 to 6 carbons, or a pharmaceutically acceptable salt of said compound.

6. The method of claim 1 wherein said RAR antagonist or inverse agonist has the chemical structure:

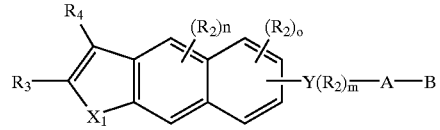

wherein $X_1$ is: $-C(R_1)_2-$, $-C(R_1)_2-C(R_1)_2-$, $-S-$, $-O-$, $-NR_1-$, $-C(R_1)_2-O-$, $-C(R_1)_2-S-$, or $C(R_1)_2-NR_1-$; and $R_1$ is independently H or alkyl of 1 to 6 carbons; and $R_2$ is optional and is independently defined as lower alkyl of 1 to 6 carbons, F, Cl, Br, I, $CF_3$, fluoro substituted alkyl of 1 to 6 carbons, OH SH, alkoxy of 1 to 10 6 carbons, or alkylthio of 1 to 6 carbons; and m is an integer between, and including, 0 and 4; and n is an integer between, and including, 0 and 2; and o is an integer between, and including, 0 and 3; and R3 is H, lower alkyl of 1 to 6 carbons, F, Cl, Br or I; and R4 is $(R_5)_p$-phenyl, $(R_5)_p$-naphthyl, $(R_5)_p$-heteroaryl where the heteroaryl group is five-membered or 6-membered and has 1 to 3 heteroatoms selected from the group consisting of O, S, and N; and p is an integer between, and including, 0 and 5; and $R_5$ is optional and is defined as independently F, Cl, Br, I, $N_2$, $N(R_8)_2$, $N(R_8)COR_8$, $N(R_8)CON(R_8)_2$, OH, $OCOR_8$, $OR_8$, CN, COOH, $COOR_8$, an alkyl group having from 1 to 10 carbons, an alkenyl group having from 1 to 10 carbons and 1 to three double bonds, alkynyl group having from 1 to 10 carbons and 1 to 3 triple bonds, or a (trialkyl)silyl or (trialkyl)silyloxy group where the alkyl groups independently have from 1 to 6 carbons; and Y is a phenyl or naphthyl group, or a heteroaryl selected from the group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups, or Y is $-CR_3=CR_3)_r-$; and r is an integer between, and including, 1 and 3; and A is $(CH_2)_q$ where q is an integer from 0–5, lower branched chain alkyl having from 3 to 6 carbons, cycloalkyl having from 3 to 6 carbons, alkenyl having from 2 to 6 carbons and 1 or 2 double bonds, alkenyl having from 2 to 6 carbons and 1 or 2 triple bonds, with the proviso that when Y is $-CR_3=CR_3)_r-$ then A is $(CH_2)_q$ and q is 0; and B is H, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, $CR_7OR_3O$, or $Si(C_{1-6alkyl})_3$, wherein $R_7$ is an alkyl, cycloalkyl or alkenyl group containing 1 to 5 carbons, $R_8$ is an alkyl group of 1 to 10 carbons or (trimethylsilyl)alkyl, where the alkyl groups has 1 to 10 carbons, or a cycloalkyl group of 5 to 10 carbons, or $R_8$ is phenyl or lower alkylphenyl, $R_9$ and $R_{10}$ independently are H, a lower alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is a divalent alkyl radical of 2–5 carbons.

7. The method of claim 1 wherein said RAR antagonist or inverse agonist has the chemical structure:

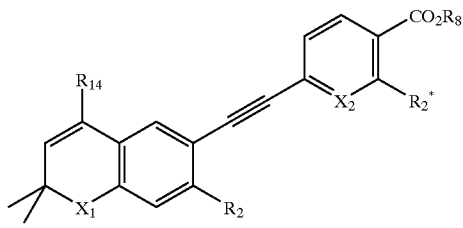

where $X_1$ is S or O;

$X_2$ is CH or N;

$R_2$ is H, F, $CF_3$ or alkoxy of 1 to 6 carbons;

$R_2$* is H, F, or $CF_3$;

$R_8$ is H, or lower alkyl of 1 to 6 carbons;

$R_{14}$ is unsubstituted phenyl, thienyl or pyridyl, or phenyl, thienyl or pyridyl substituted with one to three $R_{15}$ groups, where $R_{15}$ is lower alkyl of 1 to 6 carbons, chlorine, $CF_3$, or alkoxy of 1 to 6 carbons, or a pharmaceutically acceptable salt of said compound.

8. The method of claim 1 wherein said RAR antagonist or inverse agonist has the chemical structure:

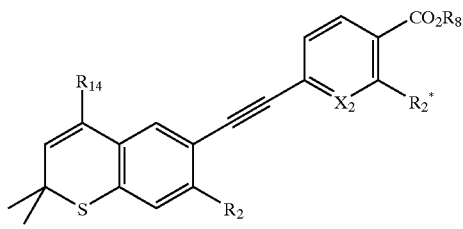

wherein $X_2$ is CH or N, and;

$R_2$ is H, F, or $OCH_3$, and;

$R_2$* is H or F, and;

$R_8$ is H, or lower alkyl of 1 to 6 carbons, and;

$R_{14}$ is selected from the group consisting of phenyl, 4-(lower-alkyl)phenyl, 5-(lower alkyl)-2-thienyl, and 6-(lower alkyl)-3-pyridyl where lower alkyl has 1 to 6 carbons, or a pharmaceutically acceptable salt of said compound.

9. The method of claim 1 wherein said RAR antagonist or inverse agonist has the chemical structure:

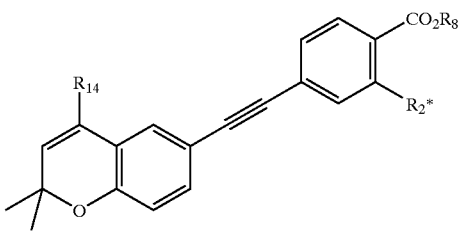

where $R_2$* is H or F;

R8 is H, or lower alkyl of 1 to 6 carbons, and $R_{14}$ is selected from the group consisting of phenyl, and 4-(lower-alkyl)phenyl, where lower alkyl has 1 to 6 carbons, or a pharmaceutically acceptable salt of said compound.

10. The method of claim 1 wherein said RAR antagonist or inverse agonist has the chemical structure:

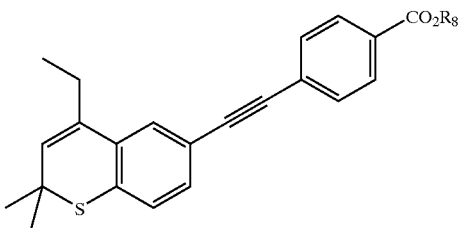

where $R_8$ is H, lower alkyl of 1 to 6 carbons, or a pharmaceutically acceptable salt of said compound.

11. The method of claim 1 wherein the RAR antagonist or inverse agonist has the chemical structure:

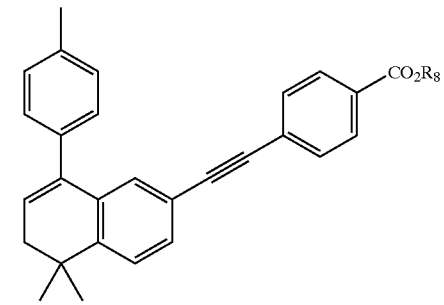

where $R_8$ is H, lower alkyl of 1 to 6 carbons, or a pharmaceutically acceptable salt of said compound.

12. The method of claim 1 wherein said RAR antagonist or inverse antagonist has the chemical structure:

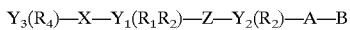

$Y_3(R_4)$—X—$Y_1(R_1R_2)$—Z—$Y_2(R_2)$—A—B

Where $Y_1$ is phenyl, naphthyl, or heteroaryl selected from the group consisting of pyridyl, thienyl, furyl, pyridazinyl, pyrimidinyl, pyrazinyl, thiazonyl, ozazolyl, imidazolyl, and pyrrazolyl, said phenyl, naphthyl, and heteroaryl groups being substituted with an $R_1$ group, and further substituted or unsubstituted with one or two $R_2$ groups;

$R_1$ is $C_{1-10}$ alkyl, 1-ademantyl, 2-tetrahydropyranoxy, trialkylsilanyloxy where alkyl has up to 6 carbons, OH, alkoxy where the alkyl group has up to 10 carbons, alkylthio where the alkyl group has up to 10 carbons, or $OCH_2OC_{1-6}$ alkyl;

$R_2$ is lower alkyl of 1 to 6 carbons, F, Cl, Br, I, $CF_3$, $CF_2CF_3$, OH, $OR_3$, $NO_2$, $N(R_3)_2$, CN, $N_3$, $COR_3$, $NHCOR_3$, COOH, or $COOR_3$;

X is $(C(R_3)_2$, S, SO, $SO_2$, O or $NR_3$;

Z is
—C≡C—,
—N=N—,
—N(O)=N—,
—N=N(O)—,
—N=CR_3—,
—CR_3=N,
—(CR_3=CR_3)_n— where n is an integer having the value 0–5,
—CO—NR_3—,
—CS—NR_3—,
—NR_3—CO,
—NR_3—CS,
—COO—,
—OCO—;
—CSO—;
—OCS—; or
—CO—CR_3=R_3—O, $R_3$ is independently H or lower alkyl of 1 to 6 carbons;

$Y_2$ is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being unsubstituted or substituted with one or two $R_2$ groups, or when Z is —$(CR_3=CR_3)_n$— and n is 3, 4 or 5 then $Y_2$ represents a direct valence bond between said —$(CR_3=CR_3)_n$ group and B;

$Y_3$ is phenyl, naphthyl, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being unsubstituted or substituted with one to three $R_4$ groups, where $R_4$ is alkyl of 1 to 10 carbons, fluoro-substituted alkyl of 1 to 10 carbons, alkenyl of 2 to 10 carbons and having 1 to 3 triple bonds, F, Cl, Br, I, $NO_2$, CN, $NR_3$, $N_3$, COOH, $COOC_{1-6}$ alkyl, OH, SH, $OC_{1-6}$ alkyl, and $SC_{1-6}$ alkyl;

A is $(CH_2)_q$ where q is from 0–5, lower branched alkyl having 3–6 carbons, cycloalkyl having 3–6 carbons, alkenyl, having 2–6 carbons and 1–2 double bonds, alkynyl having 2–6 carbons and 1 to 2 triple bonds, and B is hydrogen, COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, $CR_7OR_{13}O$, or $Si(C_{1-6}$ alkyl$)_3$, where $R_7$ is an alkyl, cycloalkyl or alkenyl group containing 1 to 5 carbons, $R_8$ is an alkyl group of 1 to 10 carbons or trimethylsilylalkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, or a pharmaceutically acceptable salt of said compound.

13. The method of claim 1 wherein said RAR antagonist or inverse agonist has the chemical structure:

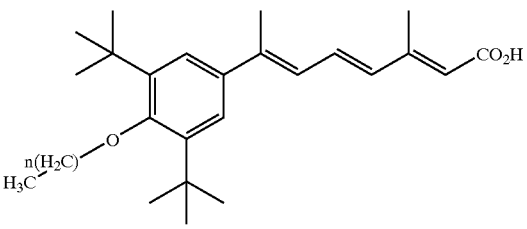

where n is an integer from 1 to 10.

14. The method of claim 1 wherein said RAR antagonist or inverse agonist has the chemical structure:

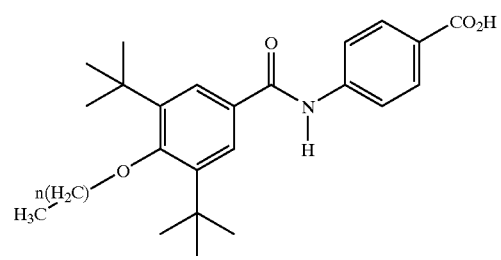

where n is an integer from 1 to 10.

15. The method of claim 1 wherein said RAR antagonist or inverse agonist has the chemical structure:

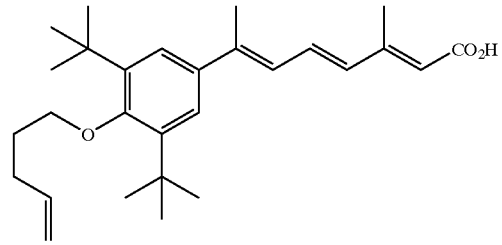

16. The method of claim 1 wherein said RAR antagonist or inverse agonist has the chemical structure:

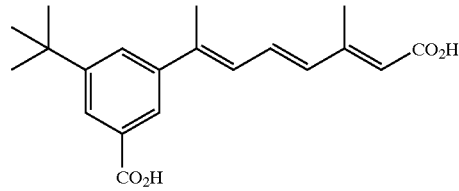

17. The method of claim 1 wherein said RAR antagonist or inverse agonist has the chemical structure:

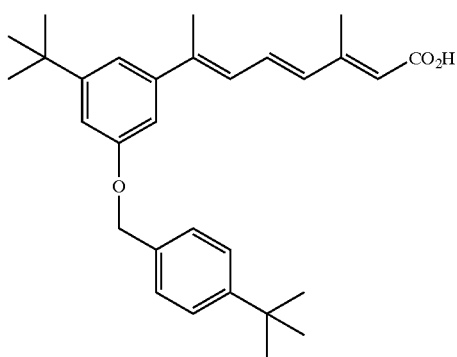

18. The method of claim 1 wherein said period of time is thirty days or more.

19. The method of claim 1 wherein said RAR antagonist or inverse agonist is administered daily.

20. The method of claim 1 wherein said RAR antagonist or inverse agonist is administered orally.

21. The method of claim 1 wherein said RAR antagonist or inverse agonist is administered topically.

22. The method of claim 1 wherein said RAR antagonist or inverse agonist inhibits transcriptional activation of two or less retinoic acid receptors selected from the group consisting of:

a) an RARα receptor;

b) an RARβ receptor; and c) an RARγ receptor.

23. A method for inhibiting spermatogenesis in a male mammal, comprising: administering to said male mammal an effective amount of a composition comprising an RAR antagonist or inverse agonist over a period of time effective to prevent conception.

* * * * *

UNITED STATES PATENT AND TRADEMARK OFFICE
CERTIFICATE OF CORRECTION

PATENT NO. : 6,521,641 B1
DATED : February 18, 2003
INVENTOR(S) : Klein et al.

It is certified that error appears in the above-identified patent and that said Letters Patent is hereby corrected as shown below:

Column 1,
Line 50, delete "n" and insert in place thereof -- than --

Column 4,
Lines 22 and 23, delete "e / o" and insert in place thereof -- basal level of RAR --

Column 5,
Line 11, delete "-($CR_1=CR_1$)n'" and insert in place thereof -- -($CR_1=CR_1$)$_{n'}$ --
Line 41, after "$CH_2OR_{11}$" add -- $CH_2OCOR_{11}$ --
Line 46, delete "trimethylsilylallyl" and insert in place thereof -- trimethylsilylalkyl --

Column 6,
Line 40, delete "tri4ower" and insert in place thereof -- tri-lower --

Column 9,
Line 3, delete "f" and insert in place thereof -- F --

Column 10,
Line 51, delete "alklthio" and insert in place thereof -- alkylthio --

Column 11,
Line 20, after "$CH_2OR_{11}$" insert -- $CH_2OCOR_{11}$ --
Line 23, delete "cycloaLkyl" and insert in place thereof -- cycloalkyl --

Column 16,
Line 24, delete "spermnatogenesis" and insert in place thereof -- spermatogenesis --

Column 17,
Line 15, delete "4-[[4ethylphenyl)" and insert in place thereof -- 4-[[4-ethylphenyl) --
Line 57, delete "thiochroman4" and insert in place thereof -- thiochroman-4 --

Column 18,
Line 53, delete "nmuol" and insert in place thereof -- mmol --
Line 13, delete "dimethyl4" and insert in place thereof -- dimethyl-4 --

Column 19,
Line 22, delete "dimethyl4" and insert in place thereof -- dimethyl-4 --

UNITED STATES PATENT AND TRADEMARK OFFICE
CERTIFICATE OF CORRECTION

PATENT NO.    : 6,521,641 B1
DATED         : February 18, 2003
INVENTOR(S)   : Klein et al.

It is certified that error appears in the above-identified patent and that said Letters Patent is hereby corrected as shown below:

<u>Column 23,</u>
Line 61, delete "mg/kglday" and insert in place thereof -- mg/kg/day --

<u>Column 30,</u>
Line 23, delete "10"
Line 36, delete "$N_2$" and insert in place thereof -- $NO_2$ --
Line 62, delete "$CR_7OR_3O$" and insert in place thereof -- $CR_7OR_{13}O$ --

Signed and Sealed this

Fifteenth Day of July, 2003

JAMES E. ROGAN
*Director of the United States Patent and Trademark Office*